US009889358B2

(12) United States Patent
Greenwalt et al.

(10) Patent No.: US 9,889,358 B2
(45) Date of Patent: *Feb. 13, 2018

(54) SYSTEMS AND METHODS UTILIZING A BALL INCLUDING ONE OR MORE SENSORS TO IMPROVE PITCHING PERFORMANCE

(71) Applicants: Jeffrey Kyle Greenwalt, Gilbertsville, PA (US); Jeffrey Neal Frye, Harleysville, PA (US); Richard Joseph Finn, Harleysville, PA (US); Thomas Jay Nace, Telford, PA (US); Aidan Conner Frye, Harleysville, PA (US); Isaac Brady Frye, Harleysville, PA (US)

(72) Inventors: Jeffrey Kyle Greenwalt, Gilbertsville, PA (US); Jeffrey Neal Frye, Harleysville, PA (US); Richard Joseph Finn, Harleysville, PA (US); Thomas Jay Nace, Telford, PA (US); Aidan Conner Frye, Harleysville, PA (US); Isaac Brady Frye, Harleysville, PA (US)

( * ) Notice: Subject to any disclaimer, the term of this patent is extended or adjusted under 35 U.S.C. 154(b) by 90 days.

This patent is subject to a terminal disclaimer.

(21) Appl. No.: 14/731,024

(22) Filed: Jun. 4, 2015

(65) Prior Publication Data
US 2016/0354666 A1    Dec. 8, 2016

(51) Int. Cl.
A63B 69/00     (2006.01)
A63B 71/06     (2006.01)
(Continued)

(52) U.S. Cl.
CPC .......... *A63B 69/0002* (2013.01); *A63B 39/08* (2013.01); *A63B 43/004* (2013.01);
(Continued)

(58) Field of Classification Search
CPC . A63B 69/00; A63B 69/0002; A63B 24/0003; A63B 71/0619; A63B 2069/0006
See application file for complete search history.

(56) References Cited

U.S. PATENT DOCUMENTS

| 5,810,685 A | 9/1998 | Willner et al. |
| 6,157,898 A | 12/2000 | Marinelli |

(Continued)

FOREIGN PATENT DOCUMENTS

| WO | 2001037945 | 5/2007 |
| WO | 2007130057 | 11/2007 |
| WO | 2008100430 | 8/2008 |

OTHER PUBLICATIONS

"Micoach Smart Ball"—Adidas.com; http://www.adidas.com/us/micoach-smart-ball/G83963.html.

(Continued)

*Primary Examiner* — Michael Dennis
(74) *Attorney, Agent, or Firm* — Robert W. Morris; Ojeiku C. Aisiku; Eckert Seamans Cherin & Mellott, LLC

(57) ABSTRACT

A ball, and in particular a baseball or softball, including one or more sensors such as accelerometers and/or inertial measurement units, and systems and methods using the same to improve a pitcher's pitching performance are described herein. In some embodiments, the ball may include one or more inertial measurement units and/or accelerometers capable of monitoring motion of the ball while it is thrown. Various types of pitches may be selected, and in response to the inertial measurement unit(s) and/or accelerometer(s) detecting certain parameters corresponding to a selected pitch, one or more indicators may be caused to perform an action. For example, one or more illuminating elements located on the ball may turn a first color in response to detecting parameters corresponding to the selected pitch.

5 Claims, 18 Drawing Sheets

(51) Int. Cl.
| | |
|---|---|
| *A63B 39/08* | (2006.01) |
| *A63B 43/00* | (2006.01) |
| *A63B 43/06* | (2006.01) |
| *G06F 19/00* | (2011.01) |
| *G09B 19/00* | (2006.01) |
| *G06Q 10/06* | (2012.01) |

(52) U.S. Cl.
CPC .......... *A63B 43/06* (2013.01); *A63B 71/0619* (2013.01); *G06F 19/3481* (2013.01); *G09B 19/0038* (2013.01); *A63B 2069/0006* (2013.01); *A63B 2071/0625* (2013.01); *A63B 2071/0658* (2013.01); *A63B 2208/0204* (2013.01); *A63B 2220/20* (2013.01); *A63B 2220/24* (2013.01); *A63B 2220/30* (2013.01); *A63B 2220/35* (2013.01); *A63B 2220/40* (2013.01); *A63B 2220/44* (2013.01); *A63B 2220/51* (2013.01); *A63B 2220/53* (2013.01); *A63B 2220/56* (2013.01); *A63B 2220/803* (2013.01); *A63B 2225/20* (2013.01); *A63B 2225/50* (2013.01); *A63B 2243/007* (2013.01); *A63B 2243/0025* (2013.01); *A63B 2243/0037* (2013.01); *A63B 2243/0054* (2013.01); *A63B 2243/0066* (2013.01); *G06Q 10/0639* (2013.01)

(56) References Cited

U.S. PATENT DOCUMENTS

| | | | |
|---|---|---|---|
| 7,014,581 B2 | 3/2006 | Ng | |
| 7,064,498 B2 | 6/2006 | Dowling et al. | |
| 7,779,686 B1 * | 8/2010 | Rothman | A63B 43/00 473/192 |
| 8,360,904 B2 | 1/2013 | Oleson et al. | |
| 8,672,782 B2 | 3/2014 | Homsi et al. | |
| 8,725,452 B2 | 5/2014 | Han | |
| 8,758,172 B2 | 6/2014 | Creguer | |
| 8,781,610 B2 | 7/2014 | Han | |
| 8,936,523 B2 | 1/2015 | Manner et al. | |
| 9,032,794 B2 | 5/2015 | Perkins et al. | |
| 2003/0166420 A1 | 9/2003 | Chou | |
| 2007/0105664 A1 | 5/2007 | Scheinert et al. | |
| 2008/0015064 A1 * | 1/2008 | Nelson | A63B 43/00 473/571 |
| 2008/0153632 A1 | 6/2008 | Flores et al. | |
| 2011/0140931 A1 | 6/2011 | Geurts et al. | |
| 2013/0085006 A1 | 4/2013 | Nilwong et al. | |
| 2013/0274040 A1 | 10/2013 | Coza et al. | |
| 2014/0045630 A1 | 2/2014 | Perkins et al. | |
| 2014/0274487 A1 | 9/2014 | Thurman | |
| 2014/0277636 A1 * | 9/2014 | Thurman | A63B 24/0021 700/91 |
| 2014/0309058 A1 | 10/2014 | San Juan | |
| 2014/0309059 A1 | 10/2014 | Minch | |

OTHER PUBLICATIONS

"94Fifty Smart Sensor Basketball Review"—Fritz Nelson; http://www.livescience.com/43410-94fifty-smart-sensor-basketball-review.html.

"Revfire"—Revfire Softball Package; http://revfire.com/a0004.html.

"Spin on Fastballs Thrown by Elite Baseball Pitchers"—Tomoyuki Nagami, Jun Morohoshi, Takatoshi Higuchi, Hiroki Nakata, Shigeto Naito, and Kazuyuki Kansue. 2011, American College of Sports Medicine, DOI: 10.12491/MSS.0b013e318220e728.

"Applying PITCHf/x And GIFs to Tanaka"—Michael Eder, "Its About the Money": http://itsaboutthemoney.net/archives/2014/01/06/applying-pitchfx-and-gifs-to-tanaka/.

"MyTrackMan"—http://trackmanbaseball.com/.

EPO—International Search Report/Written Opinion—dated Aug. 22, 2016.

* cited by examiner

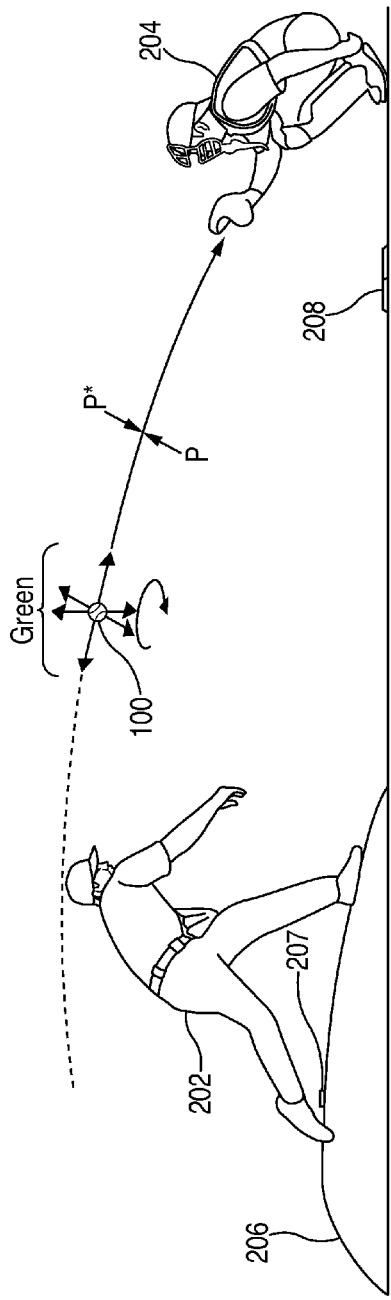
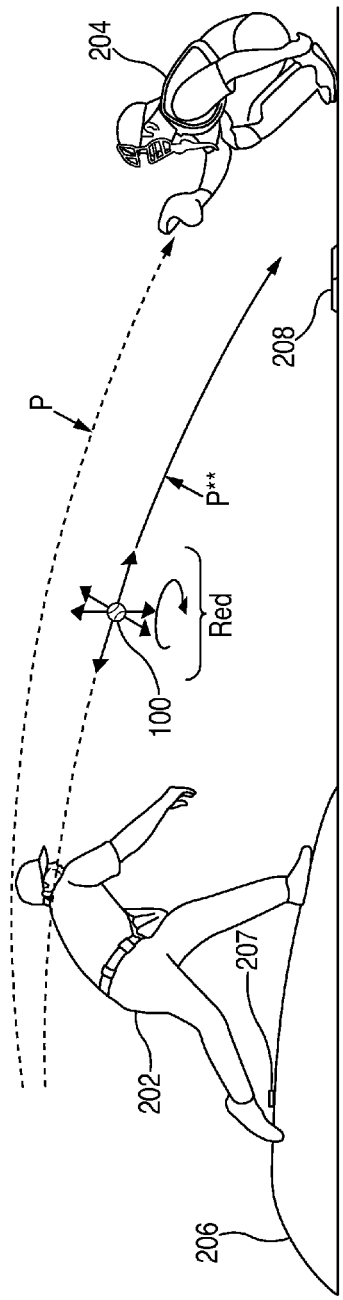

SYSTEMS AND METHODS UTILIZING A BALL INCLUDING ONE OR MORE SENSORS TO IMPROVE PITCHING PERFORMANCE

FIELD OF THE INVENTION

Various embodiments described herein generally relate to a ball, and in particular a baseball or softball, including one or more sensors such as accelerometers and/or inertial measurement units, and systems and methods using the same to improve a pitcher's pitching performance.

BACKGROUND OF THE INVENTION

Baseball, although commonly referred to as "America's Past time", is a sport that is played worldwide. From children playing little league baseball to adults playing professional baseball, the sport of baseball is played across an incredibly large age group. Baseball is also played across a broad socioeconomic and cultural spectrum, as is evident by the number of professional baseball players originating from various countries worldwide. Similarly, softball is another sport that is substantially similar to baseball in spirit, albeit a differently sized ball and field is used.

In recent years, baseball has been hampered by a rash of arm injuries suffered by pitchers, the exact cause(s) of which are still unknown. One predominate theory is incorrect biomechanics. Developed at an early age, incorrect pitching and throwing mechanics may cause unwanted and unsustainable torques and pressures on various ligaments and bones of an individual's throwing arm. Another somewhat related theory focuses on overuse by individuals at a young age. When individuals become old enough to compete at a high level, their throwing arms have been compromised due to the prolonged abuse and/or overuse of their throwing arm. With this particular theory, incorrect biomechanics may further exacerbate the problem, as the arm is even more likely to become damaged.

While there exist many baseball training aids, as well as other sport related training aids (e.g., football, basketball, and soccer), each have various drawbacks and flaws. For example, the various football, basketball, and soccer training aids currently available are unable to provide the unique feel and control of a baseball. While each of the aforementioned can be thrown, a user is unable to modify which pitch is being thrown by each due to the different size and/or shape of each sports ball. Furthermore, because the various training aids for other sports are not capable of helping an individual learn to correctly throw various types of baseball pitches, the option to change a type of pitch that is being thrown, and learn to correctly throw that baseball pitch, is not available with current training aids for other sports.

Thus, it would beneficial for there to be devices, systems, and methods for using a ball, such as a baseball or softball, including one or more sensors to improve an individual's pitching performance. Furthermore, it would be beneficial for such a ball, and a system using the ball, to provide substantially immediate feedback with regard to a quality of a pitch that an individual is attempting to throw, as well as a mechanism to allow an individual to modify a type of pitch to be thrown using the ball.

SUMMARY OF THE INVENTION

This generally relates to a ball, and in particular a baseball or softball, including one or more sensors, and systems and methods for using the same to improve an individual's pitching performance and pitching capabilities.

In one exemplary embodiment, a ball is described. The ball may include an inner spherical portion and an outer spherical portion that surrounds the inner spherical portion. The inner spherical portion, in some embodiments, may include at least one inertial measurement unit ("IMU"), at least one processor, and communications circuitry. In some embodiments, additional components, such as one or more accelerometers or sensors, memory, and/or a power source, may be included within the inner spherical portion of the ball. A first and second cover portion, which may be formed in a substantially figure eight pattern may be stitched together using a stitching material such that the first and second cover portions surround the outer spherical portion. In some embodiments, the ball may include at least one indicator, such as an illuminating element, transmitter, and/or audio producing element.

In another exemplary embodiment, another ball is described. The ball, in some embodiments, includes an inner spherical portion including at least one IMU. A first cover portion and a second cover portion each shaped in a substantially figure-eight pattern are included that cover the inner spherical portion. A stitching material is also included that forms a plurality of stitches holding the first cover portion and the second cover portion together. The stitching material further includes an illuminating material that is operable to turn a first color in response to the at least one IMU detecting a predefined motion, and turn a second color in response to the at least one IMU not detecting the predefined motion.

In yet another exemplary embodiment, a ball is described. The ball may include an inner spherical portion including at least one inertial measurement unit ("IMU"), at least one processor, and communications circuitry. The ball may also include an outer spherical portion that surrounds the inner spherical portion. In some embodiments, the ball includes a first cover portion including a first illuminating element and a second cover portion including a second illuminating element. A plurality of stitches may join the first and second cover portions together such that the first and second cover portions substantially surround the outer spherical portion.

In still another exemplary embodiment, a method for providing feedback to an individual throwing a ball is described. In some embodiments, a selection of a type of pitch for the ball to be thrown as may be received, and at least one parameter corresponding to the selected type of pitch the ball will be thrown as may be obtained. At least one sensor located within the ball may be monitored, and a determination may be made when the at least one sensor detects the at least one parameter corresponding to the selected type of pitch. In response to the at least one parameter being detected, at least one illuminating element located on a surface of the ball may be caused to turn a first color.

In still yet another exemplary embodiment, a system for assisting an individual attempting to correctly throw a type of pitch is described. The system may include a ball and a user device. The ball, in some embodiments, includes at least one IMU, at least one accelerometer, at least one baseball processor, first communications circuitry, and at least one illuminating element. The user device, in some embodiments, includes second communication circuitry, memory, a display, and at least one user device processor. The at least one user device processor may be operable to receive a selection on the display of a type of pitch for the ball to be thrown as. The processor may then retrieve, from the user device's memory, predefined threshold values for an amount of rotation and velocity for the selected type of pitch. Then, using the second communications circuitry, the predefined threshold values for the selected type of pitch may be transmitted from the user device to the first communications circuitry of the ball.

In further still another exemplary embodiment, a system for tracking and monitoring a motion of a ball is described. The system may include a ball, a first detection unit, and a second detection unit. In some embodiments, the system may also include a user device. The ball may include at least one sensor, at least one first processor, and first communications circuitry. The first detection unit may be operable to track the ball along a first plane and may be located proximate to a release area for the ball, such as a pitcher's mound. The second detection unit may be operable to track the ball along a second plane, the second plane being perpendicular to the first plane, and the second detection unit being located proximate to a receiving area for the ball, such as home plate or a batter's box.

BRIEF DESCRIPTION OF THE DRAWINGS

The above and other features of the present invention, its nature and various advantages will be more apparent upon consideration of the following detailed description, taken in conjunction with the accompanying drawings in which:

FIGS. 6B and 6C are illustrative diagrams of a ball thrown correctly and incorrectly, respectively, and corresponding feedback provided by the ball, in accordance with various embodiments;

DETAILED DESCRIPTION OF THE INVENTION

The present invention may take form in various components and arrangements of components, and in various techniques, methods, or procedures and arrangements of steps. The referenced drawings are only for the purpose of illustrated embodiments, and are not to be construed as limiting the present invention. Various inventive features are described below that can each be used independently of one another or in combination with other features. Furthermore, in at least some embodiments, liked referenced numerals refer to like parts throughout.

Figure 1:
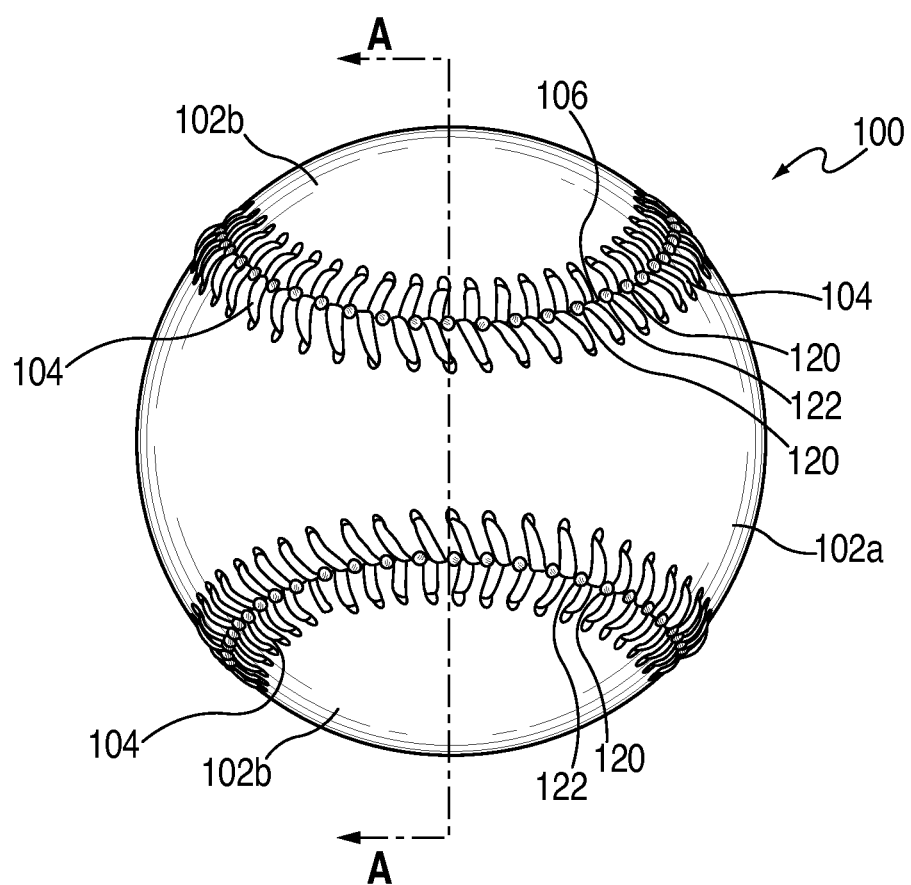
FIG. 1 is an illustrative diagram of a ball in accordance with various embodiments.

FIG. 1 is an illustrative diagram of a ball in accordance with various embodiments. Ball 100 of FIG. 1 is an exemplary ball that may be used to aid an individual while attempting to learn and execute different types of pitches. Ball 100 of FIG. 1 is, in one embodiment, substantially similar in size, weight, and feel to that of a baseball used for professional baseball games. For example, a standard baseball typically may have a circumference between 9.00 and 9.25 inches, a mass between 5.00 and 5.25 ounces, and a diameter between 2.86 and 2.94 inches. Thus, ball 100, in one embodiment, may have a substantially similar diameter, mass, and circumference. However, persons of ordinary skill in the art will recognize that any diameter, mass, and weight may be used for ball 100, and the aforementioned are merely exemplary. For example, ball 100 may correspond, in some embodiments, to a softball. A typical softball may have a circumference between 10.875 and 12.125 inches, a mass between 5.875 and 7.000 ounces, and a diameter between 3.45 and 3.86 inches. The specific parameters for the softball may vary depending on the type of softball game being played. For instance, slow pitch softball may have a slightly heavier and larger softball, whereas fast pitch softball may use a slightly smaller and lighter softball. However, in at least one embodiment, other types of sports balls, such as footballs, basketballs, tennis balls, soccer balls, golf balls, or bowling balls may be described by ball 100, and the aforementioned are merely exemplary.

Ball 100, in some embodiments, includes a first cover portion 102*a* and a second cover portion 102*b*. Cover portions 102*a* and 102*b*, which are described in greater detail below, may be substantially shaped in a figure-eight pattern such that, when sewn or stitched together, they substantially cover an inner portion of ball 100. In some embodiments, however, only one cover portion may be used to cover ball 100, so long as the single cover has a similar feel and appearance as if two cover portions were used instead. In other embodiments, however, more than two cover portions may be used to cover ball 100.

First and second cover portions 102a and 102b may be sewn or stitched together using any suitable stitching material. For example, the stitching material may be a wool yarn, a waxed thread, a plastic, or any other suitable material, or any combination thereof. In some embodiments, the stitching material may include an illuminating material such that the stitching material turns one or more colors, as described in greater detail below with regard to FIG. 3. A typical baseball includes one hundred and eight (108) stitches 104 which connect first cover portion 102a and 102b together such that substantially unitary cover surrounds any interior portion(s) of ball 100. A typical softball, however, may include eighty eight (88) stitches 104 connecting first cover portion 102a and 102b together. In some embodiments, the stitching material may be red in color, however other colors, such as black, gray, beige, or yellow, for example, may be used.

In some embodiments, ball 100 may include one or more illuminating elements 120 and 122. For example, illuminating elements 120 and 122 may be lights, light emitting diodes ("LEDs"), light emitting electrochemical cells ("LECs"), fluorescent lamps, or any other type of illuminating element, or any combination thereof. Illuminating elements 120 and 122 may, in some embodiments, each only turn a certain color. For example, illuminating elements 120 may turn a first color, such as green, while illuminating elements 122 may turn a second color, such as red. However, in other embodiments, each of illuminating elements 120 and 122 may be capable of turning to any suitable color or colors.

Illuminating elements 120 and 122 may, in some embodiments, be placed along a seam 106 formed when first cover portion 102a and second cover portion 102b are stitched together. Illuminating elements 120 and 122 may be evenly placed along seam 106 such that one or more of illuminating elements 120 or 122 are located between each stitch 104. For example, illuminating element 120 may be placed between a first and second stitch, and an illuminating element 122 may then be placed in between the second stitch and a third stitch, followed by another instance of illuminating element 120 between the third stitch and a forth stitch, and so on. As another example, illuminating element 120 may be placed between a first and second stitch, and then no illuminating element may be placed between the second and third stitch, while illuminating element 122 may be placed between the third and a fourth stitch, followed again by no illuminating element between the fourth and a fifth stitch, and so on. In some embodiments, one of each of illuminating elements 120 and 122 may be placed between each stitch 104. For example, between a first and second stitch 104 may be one of illuminating elements 120 and 122, located on either side of seam 106. Persons of ordinary skill in the art will recognize that any suitable arrangement of illuminating elements 120 and 122 between stitches 104 and along seam 106 may be used, and the aforementioned are merely exemplary. Furthermore, depending on whether ball 100 corresponds to a baseball or a softball (or any additional sports ball), the number of illuminating elements 120 and 122 will vary accordingly.

Figure 2:
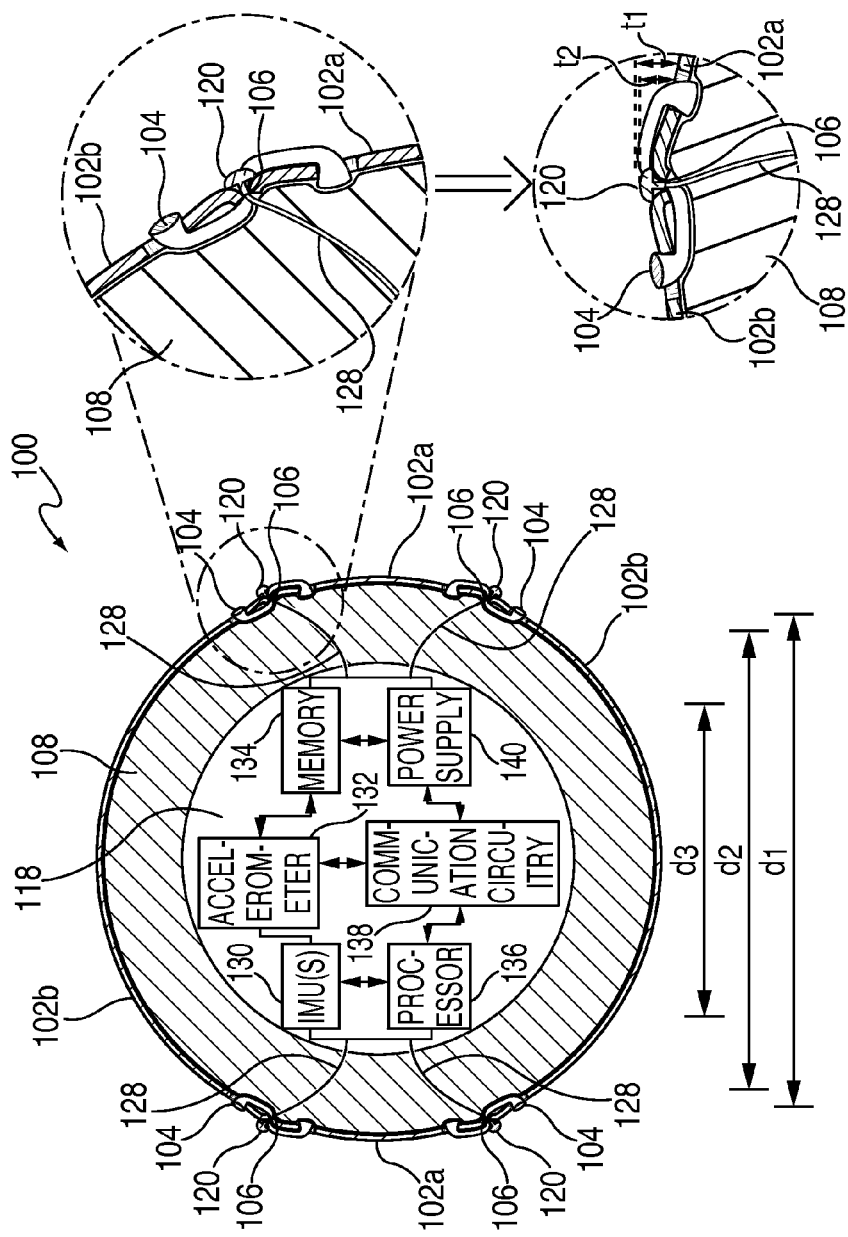
FIG. 2 is an illustrative diagram of a cross-sectional view of the ball of FIG. 1 in accordance with various embodiments.

FIG. 2 is an illustrative diagram of a cross-sectional view of the ball of FIG. 1 in accordance with various embodiments. The cross-sectional view of ball 100 of FIG. 2 is taken along line A-A of FIG. 1. As seen in FIG. 2, first and second cover portions 102a and 102b substantially surround an outer spherical portion 108 of ball 100. Seam 106 is formed at a junction of first cover portion 102a and second cover portion 102b when stitched together by a stitching material. For example, stitch 104 may couple first and second cover portions 102a and 102b together. In some embodiments, illuminating element 120 and/or illuminating element 122, may be located substantially along seam 106. For example, illuminating element 120 may be placed on an outer surface of cover portions 102a and 102b such that it resides substantially along seam 106. In some embodiments, illuminating elements 120 and 122 may extend away from cover portions 102a and 102b by a distance t2. By comparison, stitch 104 may extend away from cover portions 102a and 102b by a distance t1. Distance t1 may be greater than or equal to distance t2 in some embodiments. By having illuminating elements 120 and 122 lower as compared to stitch 104, an individual may be able to grip ball 100 without feeling illuminating elements 120 and 122. This may allow an individual to use ball 100 effectively as if it were a regular baseball.

Outer spherical portion 108, in some embodiments, is directly proximate to cover portions 102a and 102b, and resides between cover portions 102a, 102b and inner spherical portion 118, which houses various components for ball 100. Outer spherical portion 108 may, in some embodiments, be made of any suitable material, such as a rubber, yarn, wood, plastic, and/or composite, or any other material, or any combination thereof. Outer spherical portion 108 may serve multiple purposes. For example, outer spherical portion 108 may serve as a protective barrier for the various components housed within inner spherical portion 108, which are described in greater detail below. Outer spherical portion 108 may also serve to distribute mass for ball 100 such that ball 100 has a suitable mass to replicate the weight and feel of a real baseball. However, in some embodiments, outer spherical portion 108 may not be included, and inner spherical portion 118 and/or cover portions 102a, 102b may have an increased thickness and/or mass to accurately replicate the weight and feel of ball 100 to that of a regular baseball or softball.

Inner spherical portion 118 includes various components for ball 100 such that it may be used to aid an individual in accurately throwing a certain type or types of baseball or softball pitches. In some embodiments, inner spherical portion may include one or more inertial measurement units 130 ("IMUs"), one or more accelerometers 132 (e.g., multi-direction or uni-directional), memory 134, one or more processors 136, and communications circuitry 138. Inner spherical portion 118 may be a solid material, such as rubber, plastic, wood, or yarn, with one or more cavities hollowed out to insert one or more of IMU(s) 130, accelerometer(s) 132, memory 134, processor(s) 136, and communication circuitry 138. In some embodiments, however, inner spherical portion 118 may be substantially hollow. Components, such as IMU(s)) 130, accelerometer(s) 132, memory 134, processor(s) 136, and communication circuitry 138 may be affixed to an inner surface of inner spherical portion 118, or affixed to a circuit board or substrate residing within the hollow cavity of inner spherical portion 118. However, persons of ordinary skill in the art will recognize that any suitable configuration of inner spherical portion 118 may be used such that ball 100 retains the overall weight and feel of a real baseball or softball.

IMUs 130 may detect any movement of ball 100 in any direction. IMUs 130 may, in some embodiments, include one or more three-dimensional axes acceleration motion sensors, or accelerometers, capable of detecting linear accelerations along three directions (e.g., x, y, and z axis; left/right, up/down, and forward/back). IMUs 130 may also include one or more two-dimensional acceleration motion sensors operable to detect motion along two directions (e.g., x and y-axes, x and z-axes, y and z-axes). IMUs 130 may include an electrostatic capacitance accelerometer based on silicon micro-machined micro electro mechanical systems ("MEMS") technology, a piezoelectric type accelerometer, a piezoresistance type accelerometer, or any other suitable accelerometer, or any combination thereof.

In some embodiments, IMUs 130 may be capable of detecting rotation, rotational movement, angular displacement, tilt, yaw, roll, position, orientation, and motion along any path of ball 100. IMUs 130 may include linear motion sensors and non-linear motion sensors operable to detect both linear and non-linear motion of ball 100. In some embodiments, IMUs 130 may compute a gravity vector, or any acceleration due to gravity of ball 100. IMUs 130 may also include one or more gyroscopes for detecting rotational movement or spin rates of ball 100. Persons of ordinary skill in the art will recognize that any suitable technology may be used for IMUs 130, and the aforementioned are merely exemplary.

Accelerometer(s) 132 may, in some embodiments, include any suitable sensor capable of detecting an acceleration about one or more axes that ball 100 may have motion along. For example, accelerometers 132 may include a gravitational sensor, a linear motion sensor, a force sensor, a drag force sensor, and/or a Magnus force sensor. For example, a drag force sensor may be capable of detecting an amount of resistive force, or drag, felt by ball 100 as it travels along its intended path. As another example, a Magnus force sensor may be capable of detecting an amount of lift or force due to air pressure difference about ball 100 due to a rotation of ball 100. In some embodiments, IMUs 130, as previously described, may include one or more accelerometers such that one or more of the listed accelerometers 132 may not need to be included. However, in some embodiments, ball 100 may include both IMUs 130 and accelerometer(s) 132.

Memory 134 may include any suitable form of memory such as cache memory, semi-permanent memory (e.g., RAM), or any other memory type, or any combination thereof. In some embodiments, memory 104 may be used in place of and/or in addition to an external memory source or storage unit or device for storing data. Memory 134 may also include one or more storage mediums including, but not limited to, hard drives, solid state drives, flash memory, permanent memory (e.g., ROM), or any other storage type or any combination thereof.

Processor(s) 136 may include any suitable processing circuitry capable of controlling operations of one or more components within ball 100. In some embodiments, processor(s) 136 may facilitate communications between various components within ball 100. For example, processor(s) 136 may receive outputs from IMUs 130 and convey the outputs to communications circuitry 138. As another example, processor(s) 136 may receive outputs from IMUs 130 and, based on the outputs, transmit signals to illuminating elements 120 and/or 122 to turn a certain color.

Communications circuitry 138 may include any circuitry capable of connecting ball 100 with one or more devices (e.g., smart phones), one or more networks (e.g., local area networks ("LAN"), wide area networks ("WAN"), point-to-point networks, etc.), and/or to one or more servers. Communications circuitry 138 may support any suitable communications protocol including, but not limited to, Wi-Fi (e.g., 802.11 protocol), Bluetooth, radio frequency systems (e.g., 900 MHz, 1.4 GHz, and 5.6 GHz communications systems), infrared, GSM, GSM plus EDGE, CDMA, quad-band, VOIP, or any other communications protocol, or any combination thereof.

Ball 100 may also, in some embodiments, include power supply 140. Power supply 140 may be any suitable source of power capable of providing power or voltage to one or more components within ball 100. For example, power supply 140 may be a battery or capacitor operable to store voltage and produce a current to power one or more components within ball 100.

In some embodiments, ball 100 of FIG. 2 may include one or more pressure sensors that are capable of measuring and detecting an amount of pressure applied to ball 100. For example, one or more pressure sensors may be located beneath cover portions 102a and/or 102b, or within inner spherical portion 118 or outer spherical portion 118. The pressure sensors may be used to determine when contact between a user's finger(s) and ball 100 exists and when it does not exist. For example, when a pitch grips a baseball, such as ball 100, a certain amount of pressure is applied to various sections of ball 100 depending on the type of pitch intended on being thrown. The pressure sensors are operable to detect when the user has applied pressure, when the user removes pressure, and/or where and how much pressure the user has applied to ball 100.

In some embodiments, in response to detecting that the pressure sensors no longer detect any pressure on ball 100, processor(s) 136 may capture an output from IMU(s) 130 and/or accelerometer(s) 132. For example, when a pitcher releases ball 100, the outputs of IMU(s) 130 and/or accelerometer(s) 132 may be determined and recorded or stored in memory 134. In some embodiments, when the pressure sensors no longer detect pressure on ball 100, a position of ball 100 may be determined. For example, using accelerometer(s) 132, a position of ball 100 may be determined with respect to gravity, as well as a position with respect to a pitching mound. Thus, a release point for ball 100 may be determined when ball 100 is released. In some embodiments, the pressure sensors may detect when pressure on ball 100 no longer exists, and cause communications circuitry 138 to send a signal to a user device to signify that pressure has been released in order to capture positioning information of ball 100 from other detection units (e.g., detection units 1104a and 1104b of FIG. 17).

Each of cover portions 102a, 102b, outer spherical portion 108, and inner spherical portion 118 may have a diameter suitable to replicate the size and feel of an actual baseball or softball. In some embodiments, the entire ball 100 may have a diameter d1 which, in some embodiments, may be between 2.86 and 3.00 inches. In some embodiments, diameter d1 may be between 3.45 and 3.86 inches. Cover portions 102a and 102b may have a substantially similar width, which may be defined by the difference between diameter d1 and diameter d2, which corresponds to an outermost surface of outer spherical portion 108. For example, the difference between diameters d1 and d2 may range between 00.05 and 0.10 inches. Diameter d3 corresponds to a diameter of inner spherical portion 118. The thickness of outer spherical portion 118 is therefore defined by the difference between diameters d2 and d3 which, in some embodiments, may range between 00.50 and 01.00 inches for example. However, persons of ordinary skill in the art will recognize that the aforementioned values are merely exemplary.

Both inner spherical portion 118 and outer spherical portion 108 may be made of any suitable material and have any suitable thickness such that the components housed within inner spherical portion 118 are protected when ball 100 is thrown. For example, ball 100 will, in most instances, be caught be another individual (e.g., via a catcher's mitt). Inner spherical portion 118 and/or outer spherical portion 108 may provide cushion and support such that, when ball 100 is caught, no damage to the components within ball 100 occurs.

In some embodiments, ball 100 may include one or more wires or electrical connections 128 that electrically couple illuminating elements 120, 122 to one or more components within inner spherical portion 118. Electrical connections 128 may, in some embodiments, provide power and/or electrical signals to illuminating elements 120 and 122. For example, electrical connections 128 may provide power to illuminating elements 120 and 122 from power supply 140. As another example, electrical connections 128 may provide an electrical signal from processor(s) 136 that cause illuminating elements 120 and/or 122 to turn a certain color, light up at a specific intensity, change colors at a certain rate (e.g., blink), and/or not light up.

Electrical connections 128 may couple to an inner face of illuminating elements 120, 122 which resides on an outer surface of cover portions 102a or 102b. Electrical connection 128 may extend through cover portions 102a and 102b, as well as extend through outer spherical portion 108 to inner spherical portion 118. In some embodiments, electrical connections 128 may couple to one or more components located within inner spherical portion 118. For example, electrical connections 128 may couple to power supply 140, processor(s) 136, IMU(s) 130, and/or any other component, or any combination thereof. In some embodiments, one or more components within inner spherical portion 118 (e.g., power supply 140, communications circuitry 138, etc.) may be affixed to a substrate or printed circuit board. Electrical connections 128 may, in this scenario, connect to the substrate or printed circuit board.

Persons of ordinary skill in the art will also recognize that ball 100 may include one or more insulating layers (e.g., between inner and outer spherical portions 118 and 108, between outer spherical portion 108 and cover portions 102a and 102b). The insulating layers may serve to protect an individual throwing ball 100 receiving any electrical shock from an erroneously discharging element within, or on, ball 100.

In some embodiments, ball 100 may include one or more additional components such as an audio producing element (e.g., a speaker), transmitter, a bus connector, and/or any other suitable component. For example, ball 100 may include one or more additional electrical wires or connectors to electrically couple one or components together (e.g., IMUs 130 and illuminating elements 120, 122). As another example, ball 100 may include one or more speakers that may output an audible tone in response to ball 100 being thrown accurately. The audible tone generated by the speaker may be from an electrical signal outputted to the speakers. For example, in response to detecting an output from IMU(s) 130 and/or accelerometer(s) 132, processor(s) 136 may send a signal to the speakers to produce a sound indicating to a pitcher that ball 100 has been thrown correctly. As yet another example, ball 100 may include a transmitter operable to send signals to one or more additional devices such as detection units or user devices. For instance, in response to certain conditions being met by IMU(s) 130 and/or accelerometer(s) 132, processor(s) 136 may send a signal to other devices using a transmitter located within ball 100.

Figure 3:
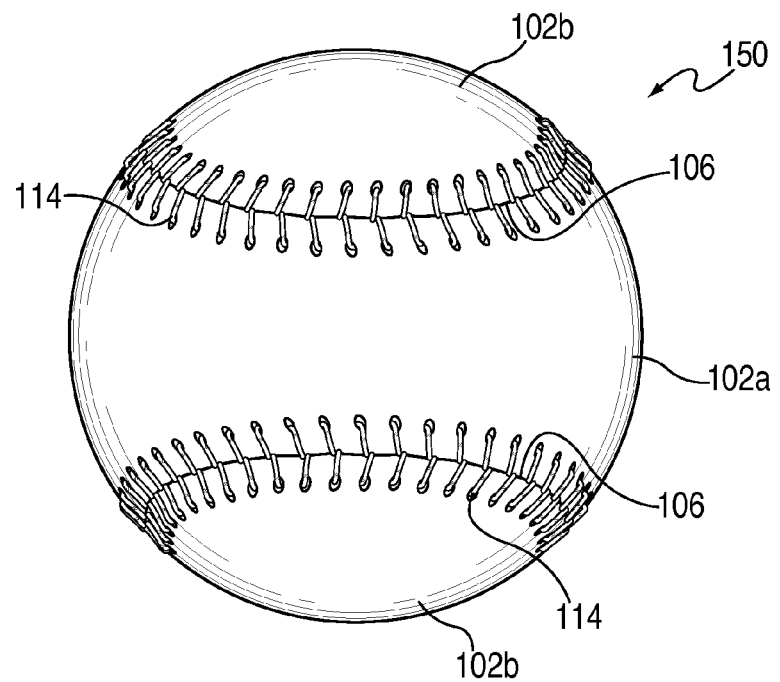
FIG. 3 is an illustrative diagram of another ball in accordance with various embodiments.

FIG. 3 is an illustrative diagram of another ball in accordance with various embodiments. In one embodiment, ball 150 may correspond to a baseball or a softball. Ball 150 of FIG. 3 is, in some embodiments, substantially similar to ball 100 of FIG. 1, with the exception that ball 150 includes stitches 114 made from a stitching material having an illuminating element included therein. For example, the stitching material of stitches 114 may be, or may include, an illuminating fiber or yarn that is coupled to one or more components within ball 150 (e.g., power supply 140), such that stitches 114 may turn different colors in response to various instructions from processor(s) 136. As another example, the stitching material of stitches 114 may be made from a combination of a non-illuminating fiber or thread and an illuminating fiber or thread, which are wound together to form a unitary thread or fiber. As yet another example, an illuminating coating may be applied to the stitching material of stitches 114 such that, when activated by battery 140 or other power supply, stitches 114 turn a certain color. As still yet another example, illuminating particulates may be integrated into the stitching material of stitches 114.

In some embodiments, one or more electrical connections, such as electrical connections 128 of FIG. 2, may couple stitching material used to form stitches 114 to power source 140 within inner spherical portion 118. For example, a copper wire may extend from a stitch 114 through outer spherical portion 108 to power supply 140. In some embodiments, however, an additional power supply may line an inner surface of cover portion 102a and/or 102b, or an outer surface of outer spherical portion 108 such that each stitch 114 may contact the power supply. The stitches may further be coupled via one or more copper wires or other electrical connections to processor(s) 136 to receive instructions for which color to illuminate based on various detected outputs from IMUs 130 and/or accelerometer(s) 132.

Figure 4:
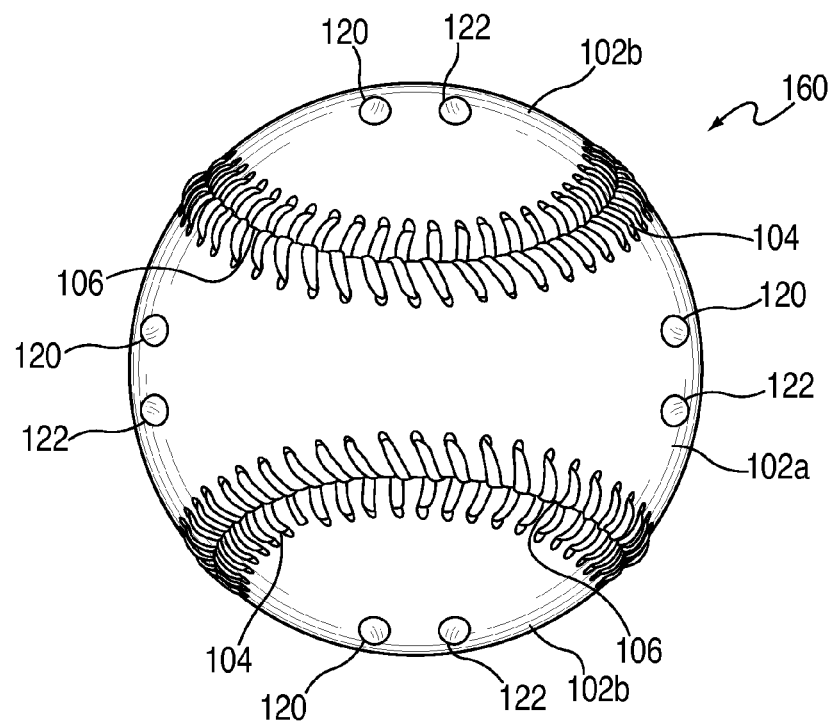
FIG. 4 is an illustrative diagram of yet another ball in accordance with various embodiments.

FIG. 4 is an illustrative diagram of yet another ball in accordance with various embodiments. In one embodiment, ball 160 may correspond to a baseball or a softball. Ball 160, in some embodiments, is substantially similar to ball 100 of FIG. 1 with the exception that illuminating elements 120 and 122 may be placed on cover portions 102a, 102b such that they are not in line with seam 106. For example, ball 160 may include eight illuminating elements 120 and/or 122, which may be distributed evenly about an exterior of ball 160. For instance, if ball 160 is taken to be a symmetrical sphere having a diameter d3 and an origin at the center of ball 160, illuminating elements 120 and/or 122 may be placed at spherical coordinates (d3, 0°, 0°), (d3, 0°, 180°), (d3, 0°, 90°), (d3, 90°, 90°), (d3, 180°, 90°), and (d3, 270°, 90°). However, persons of ordinary skill in the art will recognize that illuminating elements 120 and/or 122 may be placed at any suitable location about cover portions 102a and 102b, and the aforementioned coordinates are merely exemplary.

In some embodiments, illuminating elements 120 and 122 of ball 160 may be integrated into cover portions 102a and 102b such that the surface of cover portions 102a and 102b appears and feels smooth and consistent. This may allow an individual to properly grip ball 160 such that illuminating elements 120 and 122 do not interfere with the type of pitch the individual is attempting to throw. Furthermore, by having illuminating elements 120 and 122 integrated into cover portions 102a and 102b, the drag force effects on ball 160 may not be affected. However, in some embodiments, illuminating elements 120 and 122 may extend away from cover portions 102a and 102b, so long as the drag force effects on ball 160 due to illuminating elements 120 and 122 are negligible.

Figure 5A:
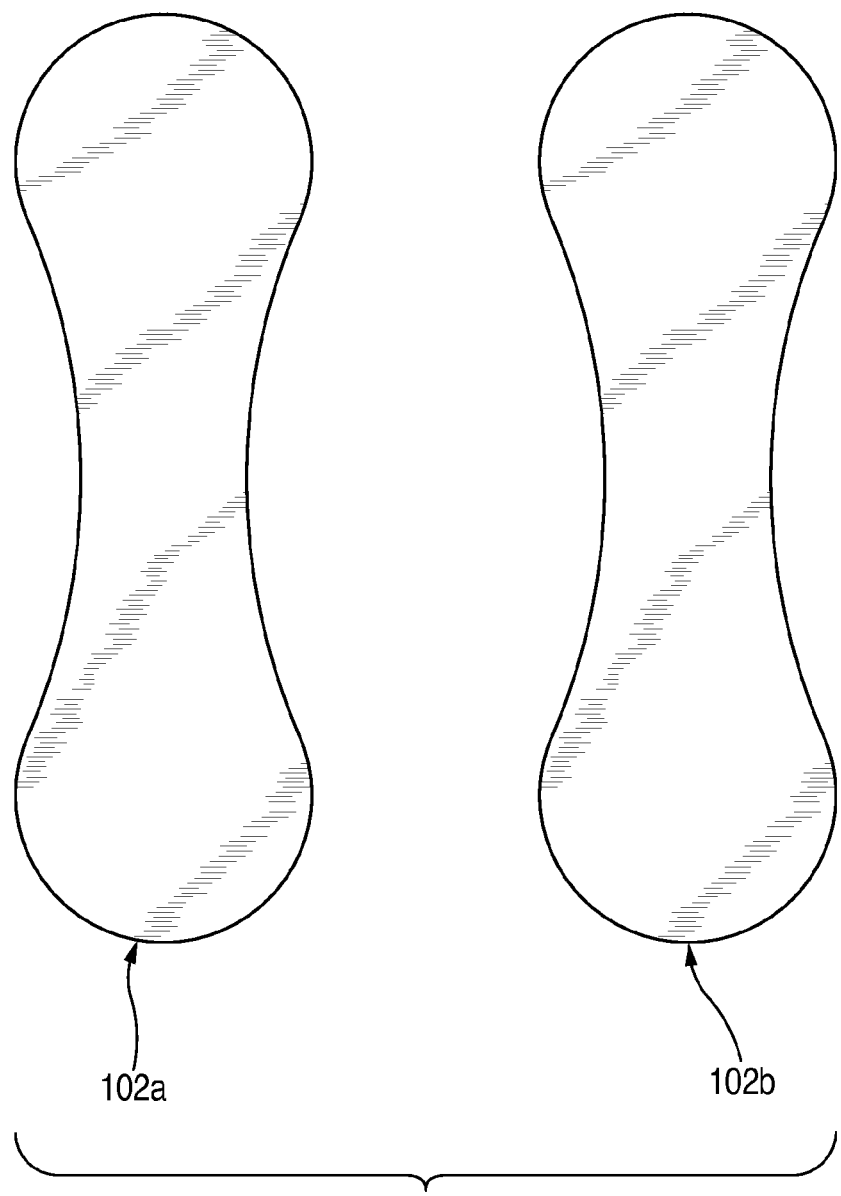
FIGS. 5A-C are illustrative diagrams of a first and second cover portion for a ball in accordance with various embodiments.
Figure 5B:
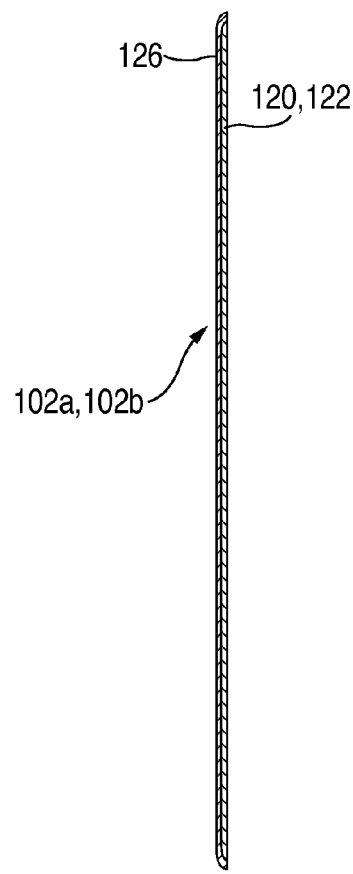
Figure 5C:
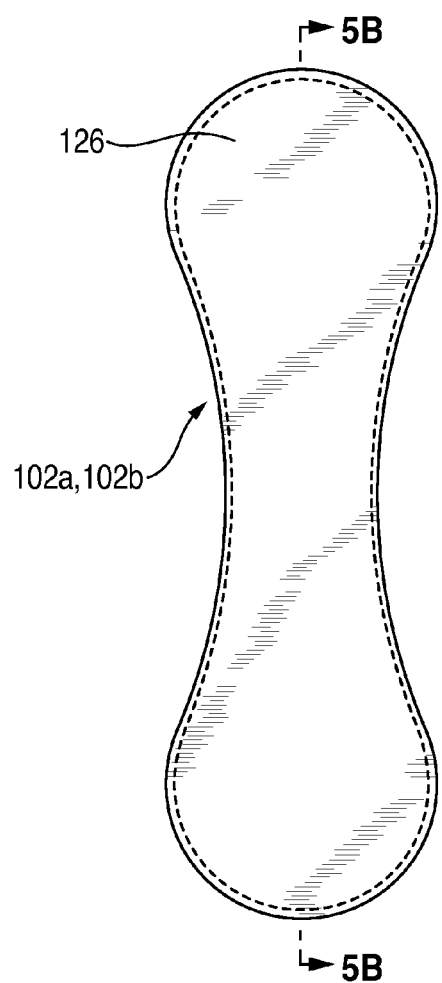

FIGS. 5A-C are illustrative diagrams of a first and second cover portion for a ball in accordance with various embodiments. As seen in FIG. 5A, first and second cover portions 102a and 102b are, in one exemplary embodiment, substantially shaped in a figure eight (8) pattern. For example, cover portions 102a and 102b may include two circular portions connected by a curved middle section. Both cover portions 102a and 102b may be substantially similar in size and shape such that, when placed on a baseball or softball, cover portions 102a and 102b substantially cover the baseball or softball. In some embodiments, however, more than two cover portions may be used to cover a baseball or softball, such as ball 100 of FIG. 1, or a baseball or softball may be covered by a single cover. In some additional embodiment, more than two cover portions 102a, 102b may be used to cover a ball, such as ball 100 of FIG. 1.

In some embodiments, cover portions 102a and 102b may be formed from an animal skin, such as a cowhide, horsehide, or leather. In other embodiments, synthetic materials, such as synthetic hides or leathers, may be used to form cover portions 102a and 102b. Other exemplary materials may include, but are not limited to, plastics, rubbers, paper, woods, threads, fabrics, or any other material, or any combination thereof. In some embodiments, cover portions 102a and 102b may include a waterproof coating or finish such that balls 100, 150, or 160 may be protected from natural elements (e.g., water).

FIG. 5B is an exemplary cross-sectional view of cover sections 102a, 102b of FIG. 5C. Cover portions 102a, 102b of FIGS. 5B and 5C may, in one embodiment, be substantially similar to cover portions 102a, 102b of FIG. 5A, with the exception that the former may include a protection cover 126 that resides on an outer surface of cover portions 102a, 102b. For example, protection cover 126 may be substantially figure-eight shaped such that it has a same shape as cover portions 102a, 102b of FIG. 5A. Protection cover 126 may be made of a plastic or other insulating material, or any other suitable material such as a hide or synthetic such that a user may be capable properly gripping ball 100, 150, and/or 160.

Protection cover 126 may cover illuminating elements 120 and 122 located on an inner portion of cover portions 102a, 102b. Illuminating elements 120, 122 may of FIG. 5B may serve to allow ball 100 to turn a first color in response to a predefined condition being met. For example, as mentioned previously, in response to detecting one or more parameters for a particularly pitch attempting to be thrown, illuminating elements 120, 122 may light up a first color indicating that ball 100 was thrown correctly. If the parameters are not detected, illuminating elements 120, 122 may light up a second color. Furthermore, in some embodiments, first cover portion 102a may light up a first color in response to the parameters being detected, whereas second cover portion 102b may light up a second color in response to the parameters not being detected.

FIG. 5C shows a substantially planar view of cover portions 102a, 102b of FIG. 5B. As seen in FIG. 5C, an outer portion of cover portions 102a, 102b includes protection cover 126. Thus, illuminating elements 120, 122 may be protected from damage by protection cover 126 such that ball 100 is not damaged if thrown incorrectly, or when caught. Illuminating elements 120, 122 may be substantially figure-eight shaped, however they may, in some embodiments, be slightly smaller than protection cover 126, as illustrated by the dashed line in FIG. 5C. However, persons of ordinary skill in the art will recognize that any shape or configuration of illuminating elements 120, 122 may be used such that cover portion 102a and/or 102b are capable of turning one or more colors.

Figure 6A:
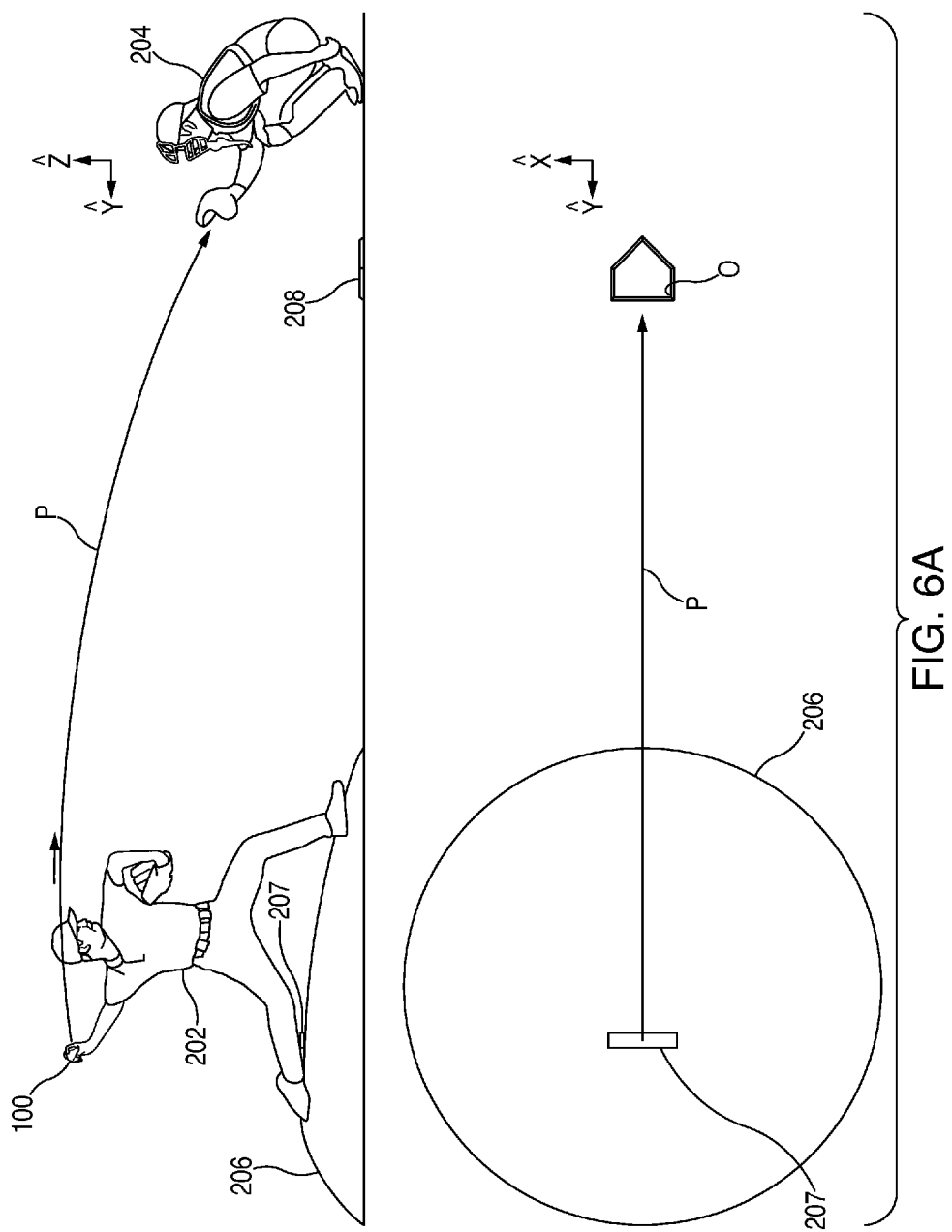
FIG. 6A is an illustrative diagram of a ball being used to throw a pitch in accordance with various embodiments.

FIG. 6A is an illustrative diagram of a ball, such as a baseball, being used to throw a pitch in accordance with various embodiments. An individual, such as a pitcher 202 may throw ball 100 to a catcher 204. Pitcher 202, when throwing ball 100, for example, may be pitching from on top of a baseball mound 206. A typical baseball mound 206 is no more than 10 inches in height above home plate 208, which, typically, is 60 feet 6 inches away from a front edge of a pitcher's plate 207. However, persons of ordinary skill in the art will recognize that this is merely one illustrative example, and mound 206 and/or plate 208 may correspond to a mound and home plate for softball, or any other type of configuration (e.g., little league, high school, etc.)

Home plate 208 is typically a five-sided structure having a front side that is closest to mound 206 and parallel to plate 207. The front side of home plate 208 is typically 17 inches, with two 8.5 inch side portions extending away from mound 206 which are connected to two 12 inch sides set at an angle such that they make a point midway with respect to the front side of home plate 208. In one illustrative example, home plate 208 may be thought of as a square having sides 17 inches long, where two isosceles triangles having sides of 8.5 inches and a hypotenuse of 12 inches are removed from a rear portion of home plate 208.

For exemplary purposes, a three-dimensional reference system is used where an origin O is located at an upper left corner of home plate 208. When ball 100 is thrown along path P, it travels in a negative y-direction. The change in vertical displacement of ball 100 from pitcher 202 to catcher 204 is change along a z-axis such that gravity is oriented in the negative z-direction. A baseball moving from a right side of pitcher 202 to a left side of pitcher 202 may be defined as a positive x-direction, referring commonly to a motion of a baseball thrown by a right-handed pitcher. However, a left-handed pitcher may have ball 100 move from a left side to a right side, thus traveling in a negative x-direction. Persons of ordinary skill in the art will recognize that the coordinate system used is merely exemplary, and other reference frames and origins may be used.

FIGS. 6B and 6C are illustrative diagrams of a ball thrown correctly and incorrectly, respectively, and corresponding feedback provided by the ball, in accordance with various embodiments. FIG. 6B shows an illustrative example of pitcher 202 throwing ball 100 correctly. In some embodiments, a user may select a pitch that ball 100 will be thrown as. For example, pitcher 202 may select a fastball. When thrown correctly, ball 100 may rotate, or spin, at a certain rate, and may move, vertically and/or horizontally, a certain amount (see Table 1). Path P illustrates an exemplary path of motion for ball 100 when thrown accurately. Path P* corresponds to an actual path of motion for ball 100 when thrown by pitcher 202. As seen by FIG. 6B, exemplary path P and actual path P* are substantially aligned such that ball 100 may be said to have proper motion for a type of baseball pitch intended to be thrown (e.g., a fastball).

In response to determining that the motion of ball 100 is correct, ball 100 may cause one or more illuminating elements, such as illuminating elements 120 and/or 122, to turn a first color. For example, in response to determining that ball 100 has moved an appropriate amount vertically and horizontally at a correct spin rate for a fastball, processor(s) 136 of ball 100 may send a signal to illuminating elements 120 and 122 to turn green. Thus, as pitcher 202 throws ball 100, he/she will receive substantially immediate feedback with regards to the accuracy of the pitch they intended to throw.

If, however, a pitcher throws ball 100 incorrectly, then ball 100 may recognize one or more of an incorrect direction of motion (e.g., vertically and/or horizontally), and/or an incorrect spin rate. In response to detecting one or more incorrect factors for a selected type of pitch, ball 100 may instruct illuminating elements 120, 122 to turn a second color. For example, if pitcher 202 intends to throw a fastball, which should follow path P if thrown accurately, along path P**, then processor(s) 136 of ball 100 may send a signal to illuminating elements 120 and/or 122 to turn red. This may indicate to pitcher 202 that ball 100 has been thrown incorrectly.

TABLE 1

| Pitch Type | Velocity (mph) | Vertical Displacement (inches) | Horizontal Displacement (inches) | Spin Rate (RPMs) |
|---|---|---|---|---|
| 4 Seam Fastball | 89-99 | (−11)-(−17) | (−3)-(−6) | 2200 or greater |
| Curveball | 72-82 | (−3)-(−7) | 2-6 | 800-1200 |
| Knuckleball | 55-70 | N/A | N/A | 20-50 |
| Changeup | 78-86 | (−2)-(−10) | (−9)-(9) | 1100-1500 |
| Splitter | 80-88 | 3-10 | (−4)-(−10) | 1100-2100 |

Each time a pitcher (or another individual) selects a type of pitch to be thrown using ball 100, certain parameters for that type of pitch may be measured to determine whether ball 100 has been thrown correctly for the selected pitch. Table 1 provides some exemplary parameters that may be stored in memory 134 on ball 100 for different pitches. Persons of ordinary skill in the art will recognize that the values listed in Table 1 for the various types of pitches are exemplary, and different values may be used or programmed, and different types of pitches may be added to or removed from Table 1.

In response to a pitch being selected, parameters for the selected pitch may be retrieved from memory 134. These parameters are then compared with outputs detected by IMU(s) 130 and/or accelerometer(s) 132 to determine whether the selected pitch has been thrown correctly. For example, if a fastball has been selected, processor(s) 136 may determine whether IMU(s) 130 has detected a spin rate for ball 100 that is greater than 2200 RPMs (revolutions per minute). If so, processor(s) 136 may send a signal to, or cause, illuminating elements 120 and/or 122 to turn a first color, such as green, indicating to the pitcher that ball 100 has been correctly thrown as a fastball. If not, processor(s) 136 may cause illuminating elements 120 and/or 122 to turn a second color, such as red, or not light up at all. This may indicate to the pitcher that they have thrown ball 100 incorrectly.

Any threshold may be set for processor(s) 136 such that, when detected, illuminating elements 120 and/or 122 are caused to illuminate or turn a certain color. For example, in some embodiments, processor(s) 136 may cause illuminating elements 120, 122 to turn a first color in response to IMU(s) 130 detecting a correct spin rate for the selected pitch. As another example, processor(s) 136 may cause illuminating elements 120, 122 to turn a first color in response to IMU(s) 130 and/or accelerometer(s) 132 detecting a correct spin rate, velocity, and horizontal displacement for a selected pitch. The number of parameters that may be required for a pitch to be "correct" may vary and may also be set by the user. For example, a novice setting may only use velocity of ball 100 to determine whether or not the selected pitch has been thrown correctly. An advanced or professional setting may, instead, require the velocity, vertical displacement, horizontal displacement, and spin rate of the selected pitch be measured or detected in order to deem the thrown pitch "correct".

Figure 7:
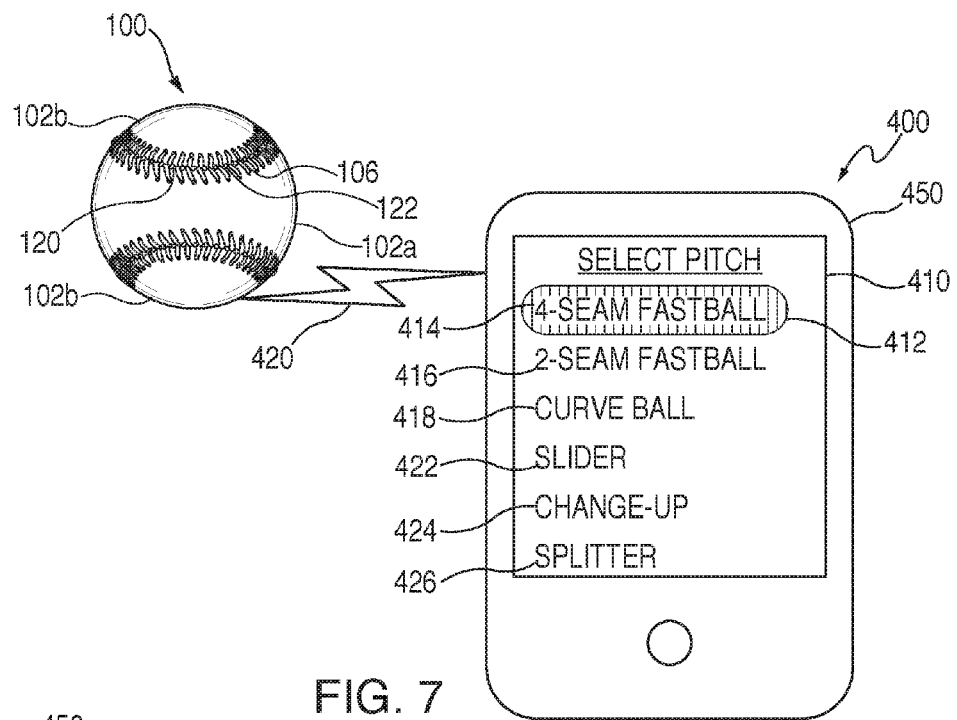
FIG. 7 is an illustrative diagram of a system including a user device and a ball in accordance with various embodiments.

FIG. 7 is an illustrative diagram of a system including a user device and a ball in accordance with various embodiments. System 400 includes ball 100, as seen in FIG. 1, and user device 450. In some embodiments, ball 150 or 160 of FIGS. 3 and 4, respectively, may be included within system 400 instead of ball 100, and the foregoing description may be applicable to such scenarios. In some embodiments, ball 100 of FIG. 7 may correspond to a baseball or a softball, and the foregoing description may be applicable to both scenarios.

In some embodiments, a user may select a type of pitch using user device 450. For example, a user may be presented with a variety of pitch types on a user interface, such as user interface 410. User interface 410 may present various pitch types that may be selected by a user operating user device 450. For example, user interface 410 may display pitches 414, 416, 418, 422, 424, and 426. A user may select one of the pitches displayed within user interface 410 by pressing a button or tapping on user interface 410 in a region where the pitch intended to be selected is displayed. For example, a user wanting to select a 4-Seam Fastball may tap or touch user interface 410 in the region of user interface 410 where pitch 414, a 4-Seam Fastball, is being displayed.

In response to tapping or touching user interface 410 to select a pitch, such as pitch 414, indicator 412 may be displayed within user interface 410. In some embodiments, indicator 412 may correspond to a displayed circle or outline surrounding the pitch (e.g., pitch 414) selected by the user. For example, indicator 412 may correspond to a highlighted portion of user interface 410 about where the selected pitch is displayed.

After the pitch has been selected on user device 450, the selection may be communicated to ball 100. For example, user device 450 may transmit information to ball 100 regarding what pitch has been selected. The selection may be transmitted across one or more networks (e.g., LAN, WAN, point-to-point), and may use any suitable communications protocol (e.g., 802.11 protocol, Bluetooth, etc.). Communications link 420 may, in some embodiments, represent the communications sent from user device 450 to ball 100. In some embodiments, however, ball 100 may be capable of transmitting communications to user device 450, as described in greater detail below.

In some embodiments, the communications transmitted to ball 100 from user device 450 may include instructions of one or more predefined values, pre-defined ranges, and/or predefined threshold values for one or more baseball pitches that are stored in memory 134 on ball 100. For example, in response to selecting pitch 414 (e.g., a 4-Seam Fastball), user device 450 may provide instructions to ball 100 to extract predefined values, ranges, and threshold values for pitch 414 that may be stored in memory on ball 100. The communications may also instruct processor(s) 136 to monitor outputs from IMU(s) 130 and/or accelerometer(s) 132 to determine if the predefined values and threshold values are detected by ball 100.

As an illustrative non-limiting example, a user may select pitch 414 on user interface 410. User device 450 may send communications to ball 100 communicating that pitch 414 has been selected. Processor(s) 136 of ball 100 may then retrieve values or ranges stored in memory 134 for pitch 414, such as velocity, vertical displacement, horizontal displacement, and/or spin rate, for example, for pitch 414. Processor(s) 136 may then monitor outputs from IMU(s) 130 and/or accelerometer(s) 132 to determine if the values for velocity, vertical displacement, horizontal displacement, and/or spin rate for pitch 414 have been detected. If they have, processor(s) 136 may then cause illuminating elements 120 and/or 122 to turn a first color, however if the values have not been detected, processor(s) 136 may instead cause illuminating elements 120 and/or 122 to turn a second color.

In some embodiments, in response to selecting a pitch on user interface 410, user device 450 may communicate values to be measured by ball 100 corresponding to the selected pitch. Based on the selected pitch 414 (e.g., a 4-Seam Fastball), user device 450 may communicate predefined values, predefined value ranges, and/or predefined threshold values, to ball 100. For example, user device 450 may communicate a predefined velocity range or threshold value for pitch 414 (e.g., between 88-99 mph or greater than 85 mph for a 4-Seam Fastball), a predefined horizontal displacement range or threshold value, a predefined vertical displacement range or threshold value, and/or a predefined spin rate range or threshold value (e.g., greater than 2200 RPMs). After receiving the information from user device 450, ball 100 may store the predefined values in memory 134. Processor(s) 136 may then, accordingly, monitor outputs from IMU(s) 130 and/or accelerometer(s) 132 to determine if any of the predefined values now stored in memory 134 are detected.

In some embodiments, as described in greater detail below, ball 100 may communicate information to user device 450 across communications link 420. For example, ball 100 may communicate information regarding one or more of the detected outputs from IMU(s) 130 and/or accelerometer(s) 132. User device 450 may receive information from ball 100 and may use this information to create or display graphics to a user regarding the quality of ball 100 as thrown for different pitches.

Figure 8:
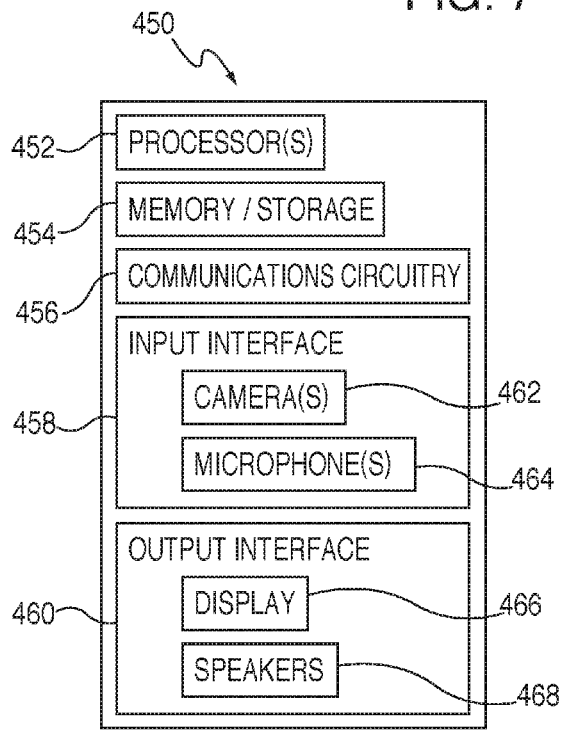
FIG. 8 is an illustrative block diagram of a user device, such as the user device of FIG. 7, in accordance with various embodiments.

FIG. 8 is an illustrative block diagram of a user device, such as the user device of FIG. 7, in accordance with various embodiments. User device 450, in some embodiments, may correspond to any electronic device or system. Various types of user devices may include, but are not limited to, portable media players, cellular telephones or smart phones, pocket-sized personal computers, laptop computers, tablet computers, and/or electronic accessory devices such as smart watches or bracelets. User device 450 may communicate with one or more additional user device, networks, servers, or balls. For example, user device 450 may communicate with ball 100 of FIG. 1, ball 150 of FIG. 3, and/or ball 160 of FIG. 4. As another example, user device 450 may send text messages or emails to other user devices across a network, or user device 450 may access one or more websites located on a server.

User device 450, in some embodiments, may include one or more processor(s) 452, memory/storage 454, communications circuitry 456, input interface 458, and output interface 460. In some embodiments, input interface 458 may include one or more cameras 462 and one or more microphones 464. Output interface 460 may also include display 466 and one or more speakers 468. Persons of ordinary skill in the art will recognize that user device 450 may include any number of components, and one or more additional components or modules may be added or omitted without deviating from the scope of the present disclosure. Furthermore, one or more components may be combined or separated (e.g., memory and storage), and multiple instances of various components are also possible, however for simplicity only one of each component is shown within user device 450.

Processor(s) 452 may, in some embodiments, be substantially similar to processor(s) 138 of FIG. 2, with the exception that the former may be capable of controlling operations and functionality on user device 450. Processor(s) 452 may facilitate communications between various components within user device 100. For example, processor(s) 452 may cause display 466 to display a certain user interface corresponding to a listing of pitches that ball 100 may throw. Processor(s) 452 may run an operating system for user device 450, applications resident on user device 450, firmware applications, media applications, and/or any other type of application, or any combination thereof that functions on, or in conjunction with, user device 450.

Memory/storage 454 may include any suitable form of memory such as cache memory, semi-permanent memory (e.g., RAM), or any other memory type, or any combination thereof. In some embodiments, memory/storage 454 may be used in place of and/or in addition to an external memory source or storage unit or device for storing data. Memory/storage 454 may also include one or more storage mediums including, but not limited to, hard drives, solid state drives, flash memory, permanent memory (e.g., ROM), or any other storage type or any combination thereof. In some embodiments, memory/storage 454 may be substantially similar to memory 134 of FIG. 2 with the exception that the former may be more robust due to a greater amount of capabilities and size of user device 450 in relation to ball 100.

Communications circuitry 456 may include any circuitry capable of connecting user device 450 to one or more additional device (e.g., laptop computers, smartphones, baseballs), one or more networks (e.g., LAN, WAN, etc.), and/or one or more servers. Communications circuitry 456 may also support any suitable communications protocol including, but not limited to, Wi-Fi (e.g., 802.11 protocol), Bluetooth, radio frequency systems (e.g., 900 MHz, 1.4 GHz, and 5.6 GHz communications systems), infrared, GSM, GSM plus EDGE, CDMA, quadband, VOIP, LTE, or any other communications protocol, or any combination thereof.

Input interface 458 may include any suitable mechanism and/or component for receiving inputs from a user operating user device 450. For example, input interface 458, in one embodiment, includes one or more cameras 462. Cameras 462 may correspond to any suitable image capturing component capable of capturing images and/or video. For example, camera 462 may capture photographs, sequences of photographs, rapid shots, videos, or any other type of image, or any combination thereof. In some embodiments, cameras 462 may be capable of capturing high-definition ("HD"), 3-D, and/or panoramic images and/or videos. In some embodiments, cameras 462 may include one or more filters or settings for images and/or video that may be captured by cameras 462 (e.g., black and white, monochromatic, fades, slow-motion, etc.). In some embodiments, user device 450 may include multiple instances of camera 462. For example, user device 450 may include a front-facing camera and a rear-facing camera. In some embodiments, one or more additional image capturing components, such as a zoom or add on filter, may be used in connection with, or instead of, camera 462 to aid in capturing images and/or videos.

Microphone(s) 464 may be any component capable of detecting and/or receiving audio signals. For example, microphone(s) 464 may include one or more sensors for generating electrical signals and circuitry capable of processing the generated electrical signals. In some embodiments, user device 450 may include multiple instances of microphone 464, such as a first microphone and a second microphone. In some embodiments, user device 450 may include multiple microphones capable of detecting various frequency levels (e.g., high/low-frequency microphones). Furthermore, in some embodiments, one or more external microphones may be connected to user device 450 and may be used in conjunction with, or instead of, microphone(s) 464.

Output interface 460 may include any suitable mechanism or component for generating outputs from a user operating user device 450. For example, display 466 may, in some embodiments, present content to a user on user device 450. Display 466 may be any size or shape, and may be located on one or more regions/sides of user device 450. For example, display 466 may fully occupy a first side of user device 450, or display 466 may only occupy a portion of a first side of user device 450. Various display types include, but are not limited to, liquid crystal displays ("LCD"), monochrome displays, color graphics adapter ("CGA") displays, enhanced graphics adapter ("EGA") displays, variable graphics array ("VGA") displays, 3-D displays, high-definition ("HD") displays, or any other display type, or any combination thereof.

In some embodiments, display 466 may be a touch screen and/or an interactive touch sensitive display screen. For example, display 466 may be a multi-touch panel coupled to processor(s) 452, and may include one or more capacitive sensing panels. In some embodiments, display 466 may also correspond to a component, or portion, of input interface 458, as it may recognize and one or more touch inputs. For example, in response to detecting certain touch inputs on display 466, processor(s) 452 may execute one or more functions for user device 100 and/or may display certain content on display 466.

Speakers 468 may correspond to any suitable mechanism for outputting audio signals. For example, speakers 468 may include one or more speaker units, transducers, or arrays of speakers and/or transducers capable of broadcasting audio signals and/or audio content to an area where user device 450, or a user, may be located. In some embodiments, speakers 468 may correspond to headphones or ear buds capable of broadcasting audio directly to a user. In yet another embodiment, one or more external speakers may be connected to user device 450, and may serve to provide audio content to a user associated with user device 450.

Figure 9A:
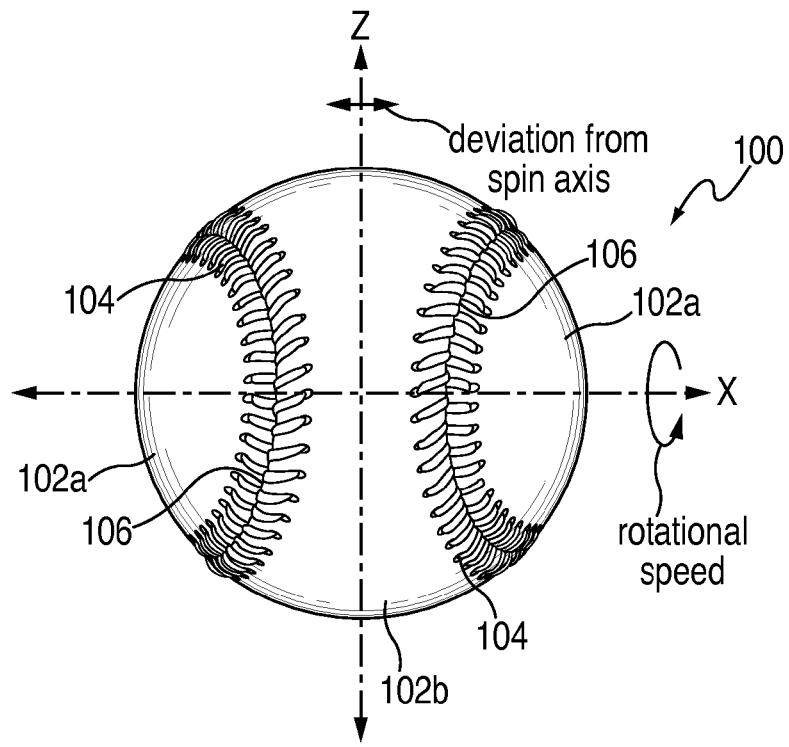
FIGS. 9A and 9B are illustrative diagrams of a ball oriented about various axes to describe a motion of the ball in accordance with various embodiments.
Figure 9B:
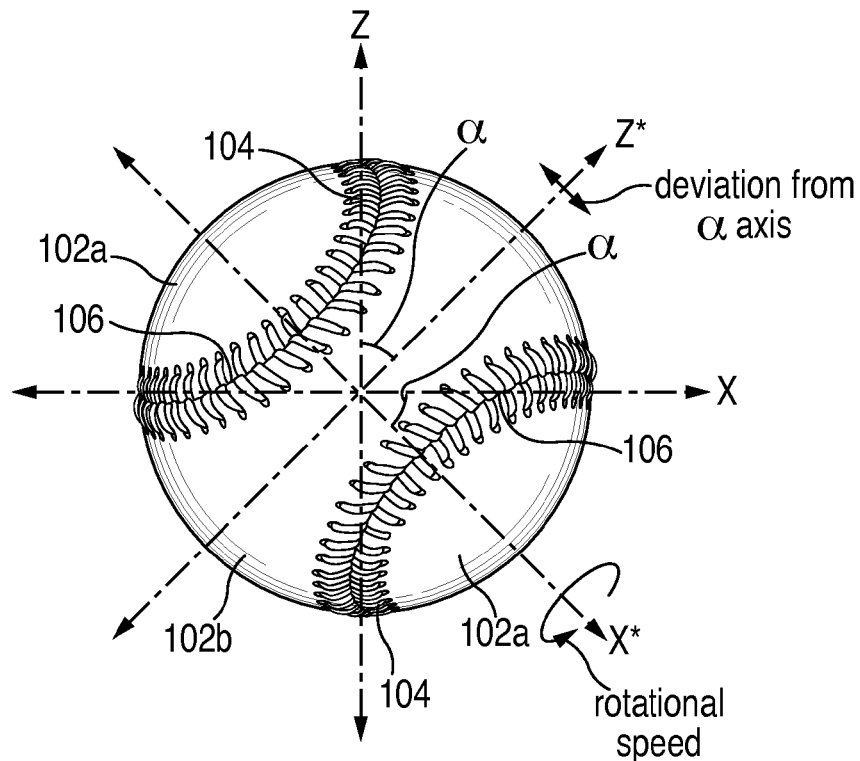

FIGS. 9A and 9B are illustrative diagrams of a ball oriented about various axes to describe a motion of the ball in accordance with various embodiments. FIG. 9A, in some embodiments, describes motion of ball 100 about two axes. For example, ball 100 may rotate about an x-axis which may run parallel to a front edge of home plate (e.g., home plate 208 of FIG. 5). Ball 100, when thrown, may rotate about the x-axis. The amount of rotation, or the spin rate, of ball 100 will depend on the type of pitch throw. For example, as seen in Table 1, a 4-Seam Fastball may have a spin rate of 2200 RPMs or greater, whereas a changeup may have a spin rate approximately between 1100 and 1500 RPMs.

In some embodiments, ball 100 may be capable of measuring an amount of deviation of ball 100 from a z-axis. For example, the z-axis, or home axis, may correspond to an axis perpendicular to the x-axis, and aligned with the direction of gravity. For certain pitches, such as a fastball, the deviation of ball 100 from the z-axis while ball 100 is in flight should be minimal. Thus, ball 100 may be capable of detecting an amount of deviation from the z-axis of ball 100. If the deviation of ball 100 from the z-axis is greater than a predefined threshold value for the selected type of pitch (e.g., a fastball), then ball 100 may determine that the pitch has been thrown incorrectly and illuminating elements 120 and/or 122 may light up a certain color (e.g., red) or may not light up at all. This may signify to the user that they have thrown ball 100 incorrectly. If ball 100, however, determines that the deviation from the z-axis is less than the predefined threshold value, then ball 100 may cause illuminating elements 120 and/or 122 to light up another color (e.g., green), signifying that ball 100 has been thrown correctly.

In some embodiments, in order for ball 100 to determine that it has been thrown correctly, more than one condition may be required. For example, in addition to determining that an amount of deviation from the z-axis is less than a predefined threshold, ball 100 may also require that the spin rate about the x-axis meet a predefined threshold value for the selected pitch. Thus, as an illustrative example, if a user attempts to throw a 4-Seam Fastball, the rotation of ball 100 about the x-axis should exceed 2200 RPMs. If this condition is met and the deviation from the z-axis is less than the predefined threshold, then ball 100 may cause illuminating elements 120 and/or 122 to light up a first color (e.g., green). However, if one or both of the conditions are not met, illuminating elements 120 and/or 122 may light up a second color, or may not light up at all.

FIG. 9B, in some embodiments, describes another exemplary motion of ball 100 about two axes. For example, ball 100 may correspond to a different pitch type, such as a curveball, having a different axis of rotation than ball 100 of FIG. 9A. In the illustrative non-limiting embodiment, the coordinate system of FIG. 9B is rotated clockwise by an angle α about the z-x plane. For example, a may correspond to an angle of 45-degrees such that the new axis of rotation of ball 100, the x*-axis, is offset from the x-axis by 45-degrees. Similarly, the new axis of deviation, the z*-axis, may be offset from the z-axis of FIG. 9A by 45-degrees.

In the scenario described above for FIG. 9B, for example, ball 100 may monitor the motion of ball 100 about the x*-axis and the z*-axis. Inertial measurement unit(s) 130 and/or accelerometer(s) 132 may, in some embodiments, receive instructions from processor(s) 136 regarding the type of pitch to be thrown, and may adjust their coordinate systems to account for that type of pitch. In this scenario, IMU(s) 130 and/or accelerometer(s) 132 may modify their coordinate system from having the axis of rotation being aligned with the x-axis and the axis of deviation or home axis aligned with the z-axis, as seen in FIG. 9A, to now having the axis of rotation aligned with the x*-axis and the home axis being the z*-axis.

Processor(s) 136 of ball 100 may monitor the outputs from IMU(s) 130 and/or accelerometer(s) 132 to determine, for a certain selected pitch (e.g., a curveball), whether or not ball 100 has rotated about the x*-axis more than a predefined threshold value for the selected pitch. For example, for a curveball, ball 100 may rotate between 1100 and 1500 RPMs about the x*-axis. If processor(s) 136 determine that IMU(s) 130 have detected a rotation of ball 100 about the x*-axis between the predefined values, then processor(s) 136 may instruct illuminating elements 120 and/or 122 to turn a first color (e.g., green). If not, processor(s) 136 may instruct illuminating elements 120 and/or 122 to turn a second color (e.g., red).

Similar to FIG. 9A, FIG. 9B may correspond to a scenario where, in order to determine that ball 100 has been thrown correctly, the deviation from axis z*-axis may be required to be less than a predefined value. For example, if ball 100 deviates from axis z*-axis more than a predefined amount (e.g., 1-2 inches or +/−10-degrees), then ball 100 may have been thrown incorrectly for the type of pitch selected to be thrown. Thus, processor(s) 136 of ball 100 may monitor the outputs of IMU(s) 130 and/or accelerometer(s) 132 to determine if ball 100 has deviated from the z*-axis by more than the predefined amount and, if it has, may cause illuminating elements 120 and/or 122 to light up a certain color (e.g., red). However, if the deviation is less than or equal to the predefined value, than processor(s) 136 may cause illuminating elements 120 and/or 122 to light up a different color (e.g., green).

In some embodiments, both conditions, the deviation from the z*-axis being less than a predefined value and the spin rate about the x*-axis being a certain amount of RPMs, may be required in order for ball 100 to be thrown "correctly". For example, if the spin rate about the x*-axis for ball 100 is between 1100 and 1500 RPMs, then ball 100 may have a proper spin rate for a certain pitch attempting to be thrown (e.g., a curveball). However, in some embodiments, in order for processor(s) 136 to cause illuminating elements 120 and/or 122 to turn a first color (e.g., green) to indicate to the user throwing ball 100 that the pitch has been thrown correctly, the deviation from the z*-axis may also be required to be less than a certain number of degrees (e.g., 10-degrees). If both of these conditions are met then processor(s) 136 may cause illuminating elements 120 and/or 122 to turn a first color (e.g., green), however if not, then processor(s) 136 may cause illuminating elements 120 and/or 122 to turn a second color (e.g., red).

Figure 10:
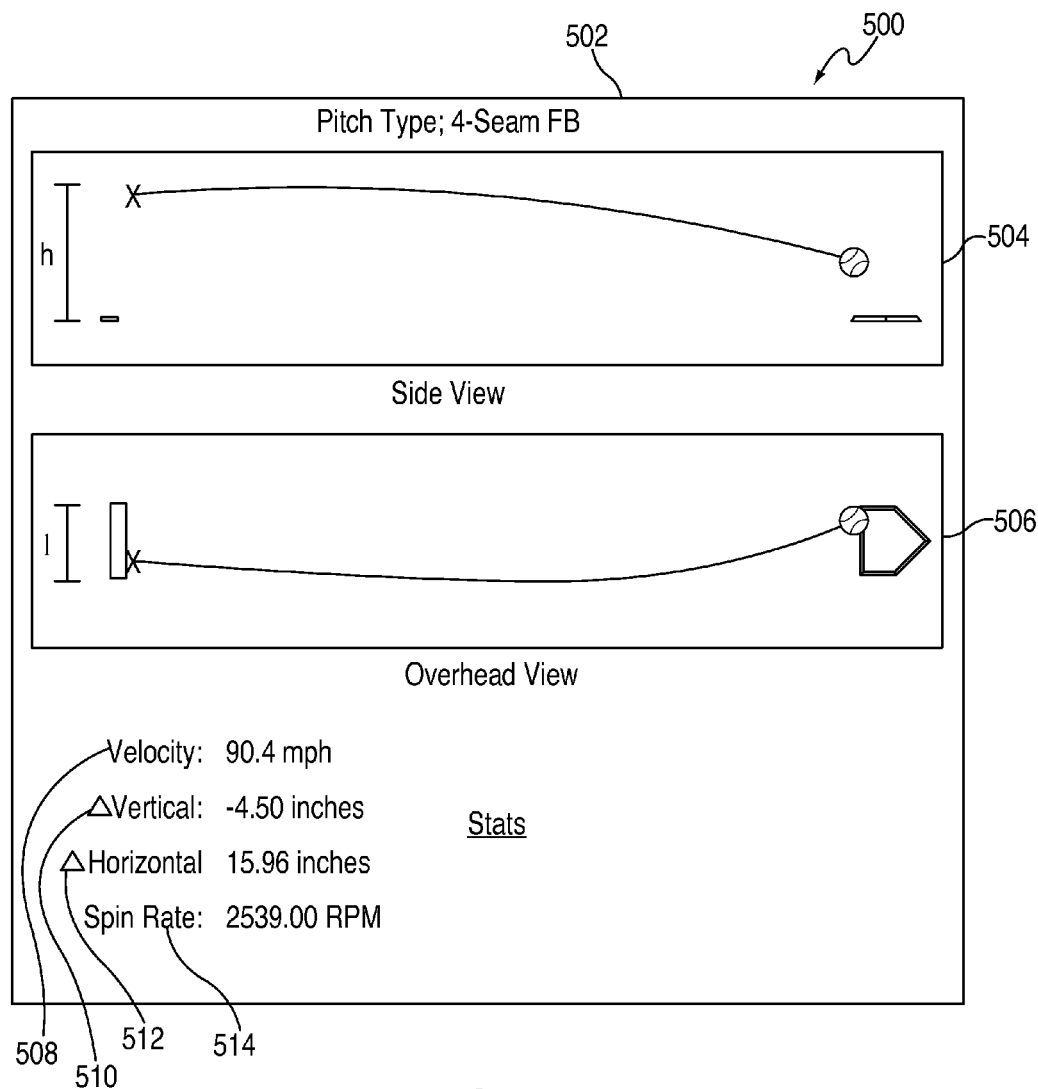
FIG. 10 is an illustrative diagram of an exemplary user interface, displayed on a user device, describing a motion and statistics of a ball in accordance with various embodiments.

FIG. 10 is an illustrative diagram of an exemplary user interface, displayed on a user device, describing a motion and statistics of a ball in accordance with various embodiments. User interface 500, in some embodiments, may be displayed on a user device, such as user device 450 of FIG. 8. User interface 500 may present content or information corresponding to a pitch that has been thrown using ball 100. For example, an individual may selected pitch 414 (e.g., a 4-Seam Fastball) on user interface 410 of FIG. 7 that ball 100 may be thrown as. After ball 100 has been thrown, information regarding the motion of ball 100 as it was thrown may be transmitted from ball 100 (e.g., via communications circuitry 138) to user device 450, and this information may be displayed within user interface 500. In some embodiments, user interface 500 may include pitch type 502, which may correspond to the type of baseball pitch selected by an individual using user interface 410. For example, a user may have selected pitch 414 (e.g., a 4-Seam Fastball), and this pitch type may be presented on user interface 500 at pitch type 502.

In some embodiments, user interface 500 may display a first graph 504 describing an exemplary side perspective view of ball 100 as it is thrown from pitching plate 207 to home plate 208. Graph 504 may show how a motion of ball 100 changes along the vertical axis (e.g., the z-axis). For example, the change in height h of ball 100, may be shown in graph 504. User interface 500 may also display a second graph 506 describing an exemplary overhead perspective view of ball 100 as it is thrown. For example, graph 100 may show how a motion of ball 100 changes along a horizontal axis (e.g., the x-axis). Both of graphs 504 and 506 may show how the motion of ball 100 changes from a catchers perspective, who sees the ball "drop" by a height h, and move from their left side to their right side by a length l.

In some embodiments, various statistics corresponding to the motion of ball 100 as it is thrown may also be displayed within user interface 500. Such statistics may include, but are not limited to, velocity 508, a change in vertical displacement 510, a change in horizontal displacement 512, and a spin rate 514. In some embodiments, the statistics presented within user interface 500 may be obtained from ball 100 as it is thrown. For example, as ball 100 is thrown, the various statistics regarding the motion of ball 100 may be sent to user device 450 and displayed within user interface 500. This may allow a user to visually see how well a pitcher is throwing ball 100 as ball 100 is being thrown. Furthermore, an individual throwing ball 100, such as a pitcher, may view the statistics associated with the pitches they throw after they complete their pitching session. Thus, if an individual throws a pitch incorrectly, they will not only be able to visually see ball 100 turn a color corresponding to an incorrect throw (e.g., red), but they will also be able to see what specifically was wrong with the pitch they threw. For example, a spin rate may not be correct for the type of pitch that an individual has attempted to throw, and the individual may be able to see the specific spin rate of the throw by viewing user interface 500, as well as the path that ball 100 took as it was thrown.

FIGS. 11A-D are illustrative diagrams of various exemplary user interfaces, displayed on a user device, describing various statistics for a type of ball pitch thrown using a ball in accordance with various embodiments. FIGS. 11A-D may, in some embodiments, show various statistics obtained by ball 100 over time for a certain type or types of pitch or pitches. For example, FIG. 11A may display a velocity of a selected type of pitch, such as a 4-Seam Fastball, over a course of time. In the illustrated example, the velocity of ball 100 may increase. As another example, FIG. 11B may display a change in vertical displacement of ball 100 as it is thrown, and how the vertical displacement change varies over time. For example, the vertical displacement for the selected pitch (e.g., 4-Seam Fastball) may, when the individual begins throwing ball 100, be approximately 1 inch. At a later point in time, when the pitcher has thrown the type of pitch more, the vertical displacement may improve and the displacement may change to approximately −4 inches (e.g., with respect to origin O).

Figure 11A:
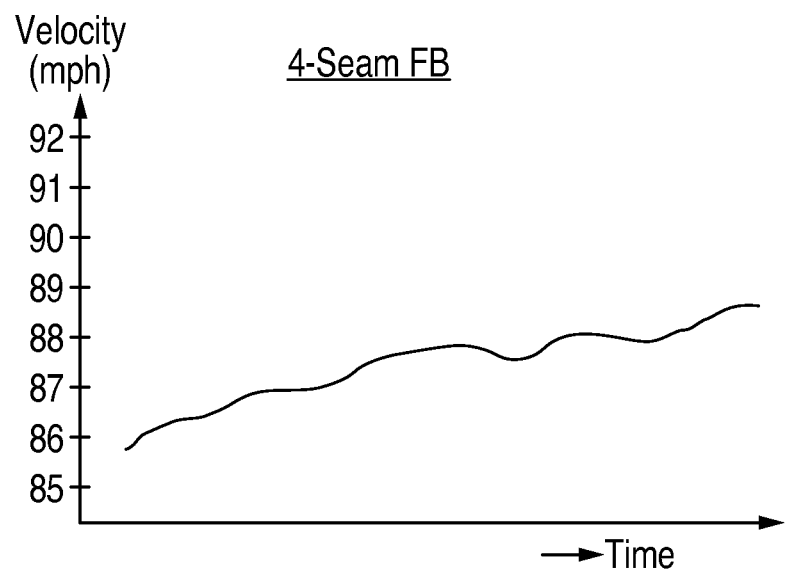
FIGS. 11A-D are illustrative diagrams of various exemplary user interfaces, displayed on a user device, describing various statistics for a type of ball pitch thrown using a ball in accordance with various embodiments.
Figure 11B:
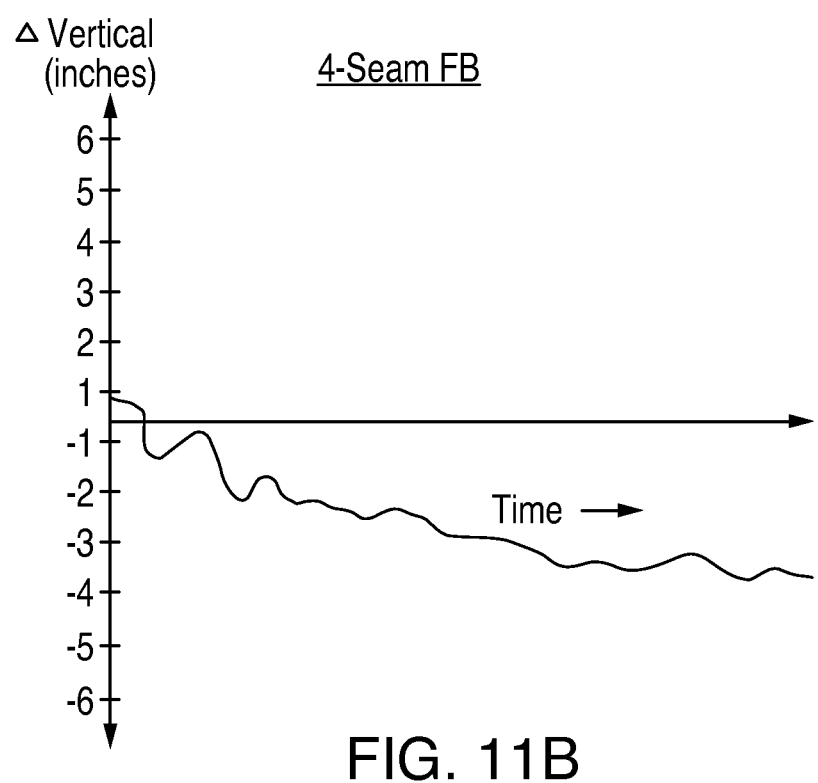
Figure 11C:
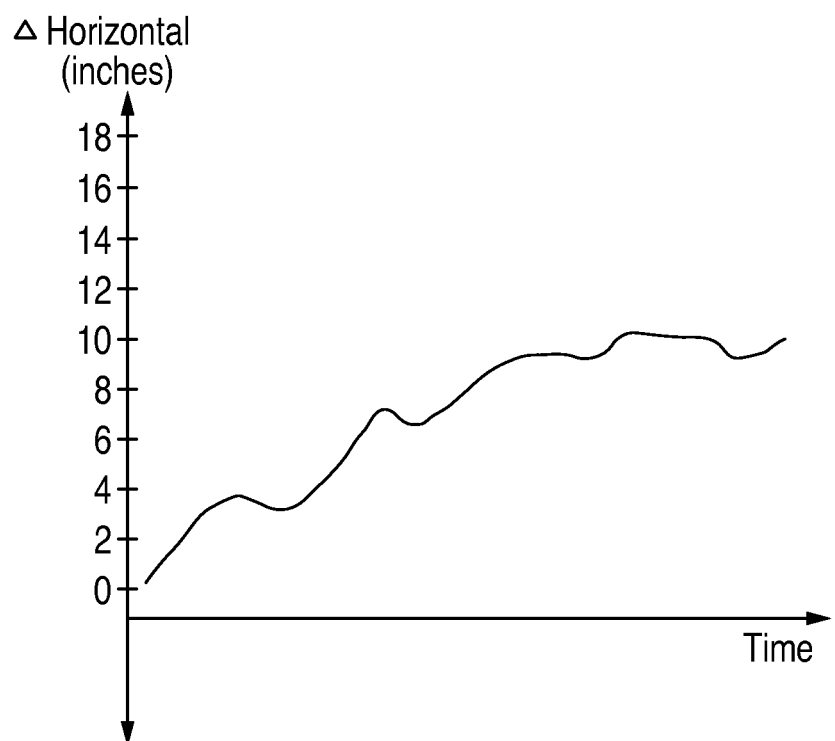

Similarly, over time, the change in horizontal displacement for a certain pitch, such as the 4-Seam Fastball, may vary, as seen in FIG. 11C. As a pitcher throws more and more 4-Seam Fastballs, the change in horizontal displacement may increase from initially having 0 inches of horizontal displacement to having 10 inches of vertical displacement, for example.

Figure 11D:
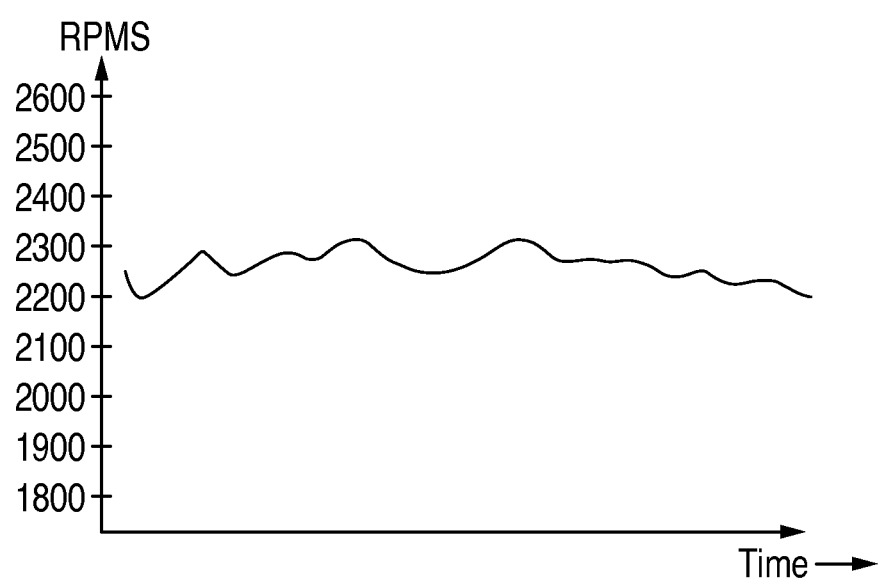

Further still, the spin rate of ball 100 for the selected pitch may change over time or may stay fairly consistent, as seen in FIG. 11D. In some embodiments, a spin rate for a 4-Seam Fastball may be greater than 2200 RPMs in order to be considered a properly thrown 4-Seam Fastball. Initially, a pitcher may throw a 4-Seam Fastball at a spin rate less than 2200 RPMs, however, over time, the pitcher may improve their ability to throw a 4-Seam Fastball such that the spin rate is consistently 2200 RPMs or greater, as seen in FIG. 11D.

Each of FIGS. 11A-D may be displayed on a user interface, such as user interface 500, for each type of pitch that a pitcher may throw, and for a total amount of time that the pitcher has been throwing that pitch. For example, a version FIGS. 11A-D may be presented for each different type of pitch that ball 100 may be thrown as. A user may select which pitch they want to view, and the corresponding plots (e.g., FIGS. 11A-D) may be presented for that pitch. Furthermore, a time period for FIGS. 11A-D may be modified by a user such that any time period for a pitch may be displayed. For example, a user may view FIGS. 11A-D for a single session of pitching, a week of pitching sessions, a month of pitching sessions, and/or a comprehensive session of every pitching session that ball 100 has been used for. Thus, an individual may see how their velocity for throwing a 4-Seam Fastball, for instance, has changed from the time that they begin throwing ball 100 until the present.

Figure 12:
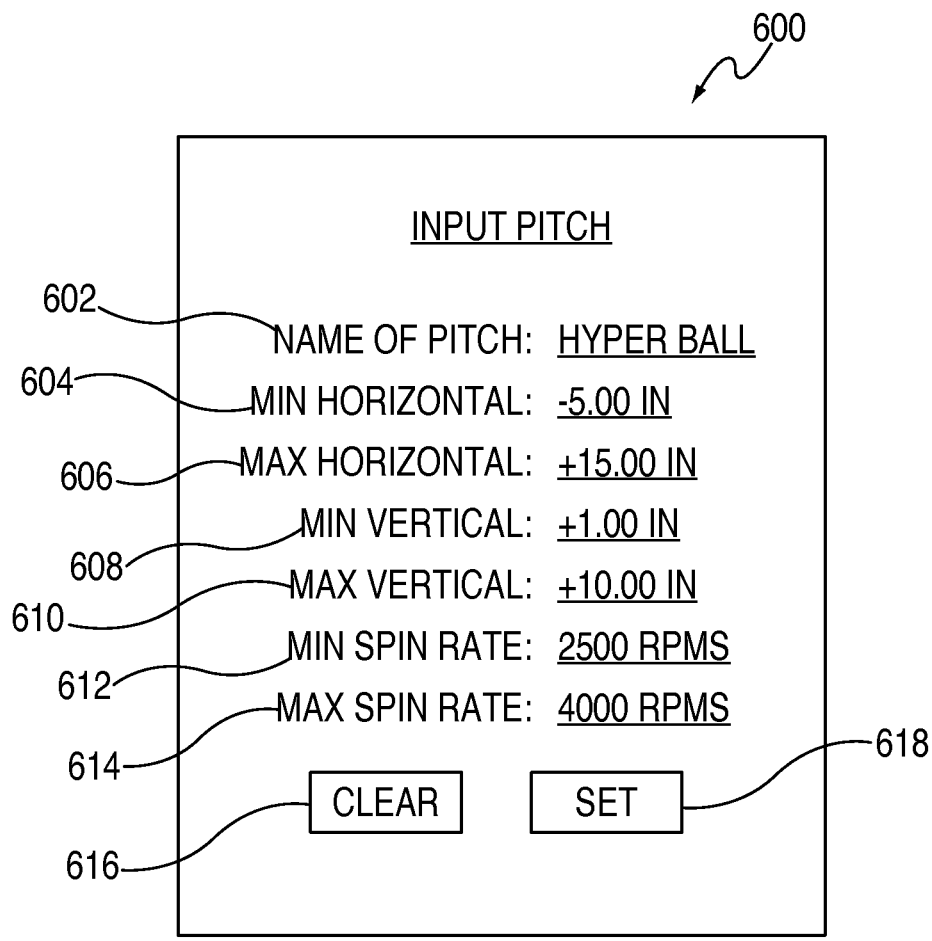
FIG. 12 is an illustrative diagram of an exemplary user interface displayed on a user device for creating parameters for a pitch to be thrown by a baseball in accordance with various embodiments.

FIG. 12 is an illustrative diagram of an exemplary user interface displayed on a user device for creating parameters for a pitch to be thrown by a ball in accordance with various embodiments. User interface 600, in some embodiments, includes a variety of options for a user to select for a pitch that they will throw using ball 100. For example, a user may decide to throw a new pitch that is not already loaded or stored on ball 100 and/or user device 450. As another example, a user may decide to modify one or more parameters of a certain pitch already stored on user device 450 and/or ball 100. In this particular scenario, the user may select a pitch already listed on a user interface (e.g., user interface 400) displayed on their user device, such as pitches 414, 416, 418, 422, 424, and/or 426, and modify one or more parameters for that pitch. This may allow the user to customize a certain pitch to correspond to the user's personal settings. As an illustrative example, the user may decide to modify the velocity for a 4-Seam Fastball from being between 88 and 98 mph, to now be 80-90 mph.

User interface 600 may, in some embodiments, include name of pitch option 602. Name of pitch option 602 may allow a user to name a pitch that they will be creating. The new pitch may, for example, be a modified version of a pre-existing pitch, or the pitch may be a brand-new pitch not based on a pre-existing pitch. A user may use any suitable name for any pitch being created or modified. For example, a user may create a new pitch named "Hyper Ball", and that name may be presented within a user interface (e.g., user interface 410) displaying a list of selectable pitches for a user to throw ball 100 as after a user has selected the parameters for the new pitch.

User interface 600 may, in some embodiments, include minimum and maximum horizontal displacement options 604 and 606, respectively. Options 604 and 606 may allow a user to select a minimum and a maximum amount of horizontal displacement, respectively, that the new or modified pitch being created should have. For example, for a new pitch called "Hyper Ball", the minimum horizontal displacement may be −5.00 inches (with respect to origin O of home plate 208), whereas the maximum horizontal displacement may be +15.00 inches. If an individual throws ball 100 such that the horizontal displacement of ball 100 is between −5.00 and +15.00 inches, then processor(s) 136 of ball 100 may determine that the ball 100 has correct horizontal displacement for a Hyper Ball pitch. Accordingly, processor(s) 136 may instruct illuminating elements 120 and/or 122 on ball 100 to turn a first color (e.g., green) to indicate to the user that he/she has thrown ball 100 correctly. If processor(s) 136, however, determine that ball 100 has, when thrown, a horizontal displacement exceed −5.00 inches or +15.00 inches then processor(s) 136 may determine that the individual has thrown ball 100 incorrectly, and thus instruct illuminating elements 120 and/or 122 to turn a second color (e.g., red).

User interface 600 may also include minimum and maximum vertical displacement options 608 and 610, respectively. Options 608 and 610 may, in some embodiments, be substantially similar to options 604 and 606, with the exception that the former may apply to an amount of vertical displacement.

User interface 600 may further, in some embodiments, include minimum and maximum spin rate options 612 and 614, respectively. Options 612 and 614 may correspond to a minimum and maximum spin rate of ball 100 for the created or modified pitch. For example, a Hyper Ball may have a spin rate between 2500 RPMs and 4000 RPMs. If processor(s) 136 on ball 100 determine that IMU(s) 132 have detected a spin rate between 2500 and 4000 RPMs then processor(s) 136 may cause illuminating elements 120 and/or 122 to turn a first color, indicating that ball 100 has been thrown correctly. If the spin rate of ball 100, however, is less than 2500 RPMs or greater than 4000 RPMs, for example, then processor(s) 136 may determine that ball 100 has not been thrown with an appropriate spin rate for a Hyper Ball, and therefore processor(s) 136 may cause illuminating elements 120 and/or 122 to turn a second color (e.g., red), indicating that ball 100 has been thrown incorrectly for the intended pitch type.

Persons of ordinary skill in the art will recognize that any value may be given to each option 604-614, and the aforementioned are merely exemplary. Furthermore, any unit (e.g., inches, millimeters, centimeters, feet, etc.) may be used, and any reference frame may be used. Still further, persons of ordinary skill in the art will recognize that any number of conditions may be used to classify a pitch as being thrown "correctly". For example, the horizontal displacement, vertical displacement, and spin rate may each be required to be within the set ranges for a thrown pitch to be classified as being correctly thrown. As another example, only the spin rate being within the set ranges for a thrown pitch may be required for classifying the pitch as being correctly thrown. In some embodiments, a user may set, prior to throwing ball 100, which criteria/parameters are to be used.

After a user has selected values for options 602-614, the user may finalize the selections by selected set option 618. By selecting set option 618, memory/storage 454 of user device 450 may store these parameters and pitch name. When a user is then presented with user interface 410, however, the newly created or modified pitch (e.g., Hyper Ball) may also be presented. In response to selecting this pitch, the parameters may be transmitted to ball 100. Ball 100 may then monitor the outputs of IMU(s) 130 and/or accelerometer(s) 132 to determine whether or not ball 100 has been thrown correctly for the selected pitch type. However, if a user decided to erase, or clear, the setting inputted in user interface 600, a user may select clear option 616, which may clear the values for a particular pitch.

Figure 13:
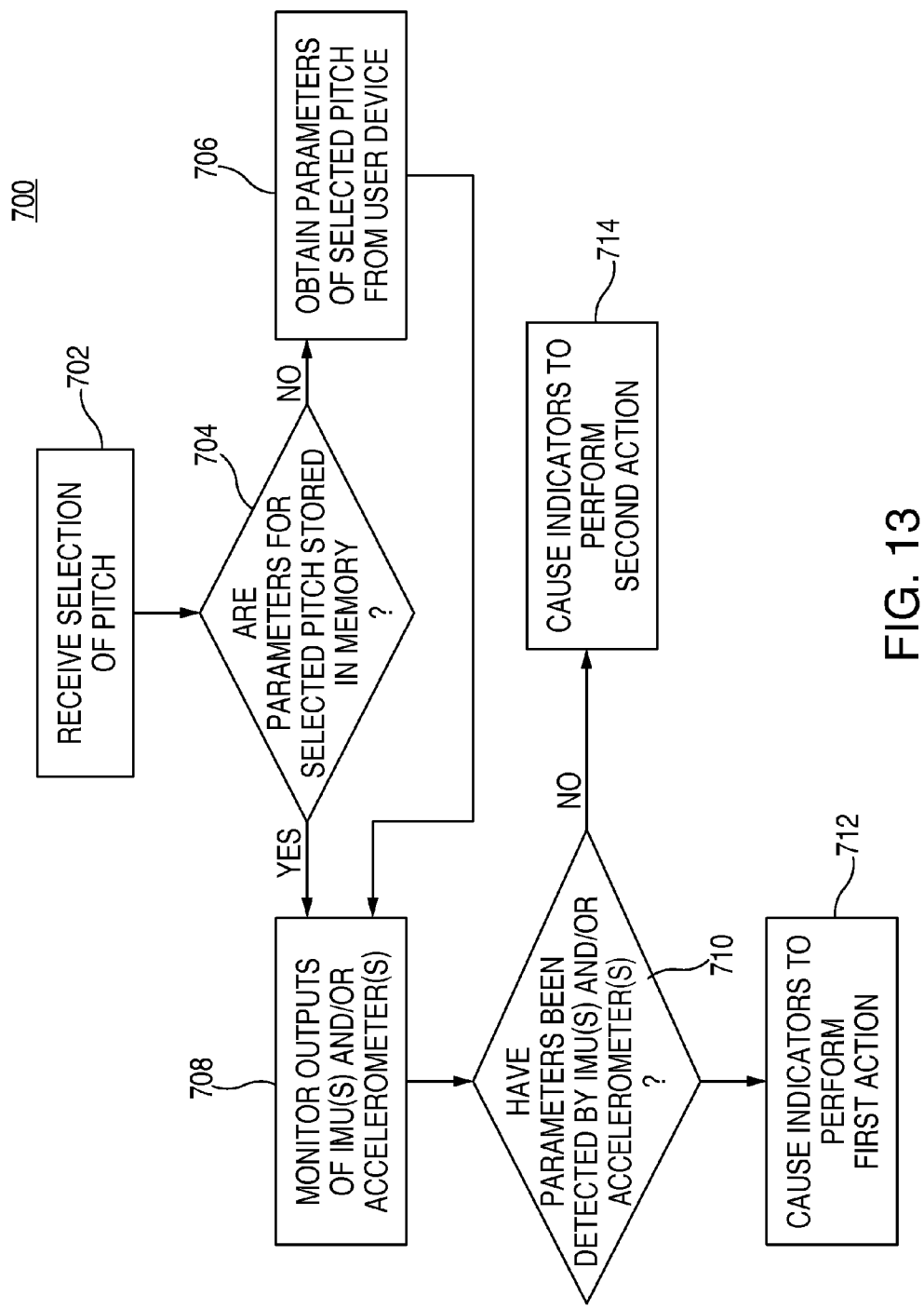
FIG. 13 is an illustrative flowchart of an exemplary process for providing feedback to a user throwing a ball in accordance with various embodiments.

FIG. 13 is an illustrative flowchart of an exemplary process for providing feedback to a user throwing a ball in accordance with various embodiments. Process 700 may begin at step 702. At step 702, a selection of a pitch that ball 100, such as a baseball or softball, will be thrown as may be received. For example, a user may select a pitch on their user device (e.g., user device 450), and the pitch that is selected may be communicated to ball 100.

At step 704, a query may be run to determine whether ball 100 has the parameter values for the selected pitch stored in memory. For example, a user may select pitch 414 on user device 450. In response to receiving the selection of pitch 414 on ball 100, processor(s) 136 may determine whether or not the parameters (e.g., velocity, horizontal/vertical displacement, spin rate) for selected pitch 414 are stored within memory 134 on ball 100.

If, at step 704, it is determined that the parameters for the selected pitch are not stored in the baseball's memory, then process 700 proceeds to step 706. At step 706, the parameters for the selected pitch are obtained from the user device. For example, if a new baseball pitch, such as "Hyper Ball" described in FIG. 12, is selected, the parameter values set for this pitch may be transmitted to ball 100 and stored in memory 134 on ball 100.

If, however, at step 704 it is determined that the parameters for the selected pitch are stored in memory on ball 100, the process 700 may proceed to step 708. At step 708, outputs from one or more IMU(s) and/or accelerometers on ball 100 (e.g., IMU(s) 130 and accelerometer(s) 132) may be monitored. For example, an output from IMU(s) 130 on ball 100 may be monitored while ball 100 is being thrown. In some embodiments, IMU(s) 130 and/or accelerometer(s) 132 are capable of measuring/detecting a velocity of ball 100, motion of ball 100, such as horizontal and/or vertical displacement, and spin rate of ball 100 about a rotational axis. In yet some additional embodiments, IMU(s) 130 and/or accelerometer(s) 132 may be operable to measure a position (e.g., height and location) with respect to a fixed origin, such as a corner of home plate, of ball 100 from its starting point to its end point.

At step 710, a determination of whether or not the parameters stored in memory and/or obtained have been detected by the IMU(s) and/or accelerometer(s) on the ball may be made. For example, for a 4-Seam Fastball, the velocity of ball 100 may be between 88-98 mph, and the spin rate of ball 100 may be greater than 2200 RPM. IMU(s) 130 and accelerometer(s) 132 may, for example, monitor the outputs of IMU(s) 130 and accelerometer(s) 132 to determine whether or not ball 100 has a velocity between the desired range and/or if ball 100 has the desired spin rate associated with a 4-Seam Fastball.

If, at step 710, it is determined that ball 100 has detected the parameters for the selected pitch, then process 700 proceeds to step 712. At step 712, processor(s) 136 on ball 100 may cause one or more indicators to perform a first action. For example, ball 100 may include one or more illuminating elements 120, 122, which may to turn a first color in response to parameters being detected for the selected pitch. For example, if processor(s) 136 determine that ball 100 has an appropriate spin rate for a 4-Seam Fastball, it may cause illuminating elements 120 and/or 122 to turn a first color, such as green. By turning green, an individual throwing ball 100 may see that they have thrown ball 100 correctly for the type of pitch they are intending to throw. As another example, the one or more indicators may correspond to an audio producing element. In response to detecting the parameters for the selected pitch, the audio producing elements, such as a speaker or transducer, may output a first audible tone or sound that the user may hear indicating that the pitch has been thrown correctly.

However, if at step 710, it is determined that ball 100 has not detected the parameters for the selected pitch, then process 700 may proceed to step 714. At step 714, processor(s) 136 of ball 100 may cause one or more indicators located on ball 100 to perform a second action. For example, ball 100 may include illuminating elements 120 and/or 122, and may turn a second color, such as red. This may indicate to the user that they have thrown ball 100 incorrectly for the type of pitch selected from step 702. Thus, a user may be able to recognize almost immediately, whether they have accurately thrown ball 100 correctly, depending on the type of pitch intended of being thrown. Furthermore, the visual feedback provided to the individual throwing ball 100 (e.g., the pitcher), may allow the individual to correct one or more aspects of their throwing motion so that they may attempt to correctly throw ball 100. As another example, as described above, the one or more indicators may correspond to one or more audio producing elements. In response to determining that ball 100 has been thrown incorrectly, the audio producing elements, such as speakers or transducers, may output a second audible tone or sound that the user may hear, indicating to the user that they have thrown ball 100 incorrectly for the selected pitch. In some embodiments, however, the one or more audio producing elements may not output an audio tone or sound in response to ball 100 being thrown incorrectly.

However, in yet another embodiment, ball 100 may include both illuminating elements and audio producing elements. For example, in response to determining that ball 100 has been thrown correctly, illuminating elements 120, 122 may turn a first color and one or more audio producing elements may output a first sound. Thus a user may receive both visual and audible feedback signifying that ball 100 has been thrown correctly. However, in response to determining that ball 100 has been thrown incorrectly, illuminating elements 120, 122 may turn a second color and one or more audio producing elements may output a second sound. Thus a user may receive both visual and audible feedback signifying that ball 100 has been thrown incorrectly. However, persons of ordinary skill in the art will recognize that any other indicator may be included with ball 100, and thus any action for that indicator may be caused to occur in response to determining that the parameters for a selected pitch have been detected.

Figure 14:
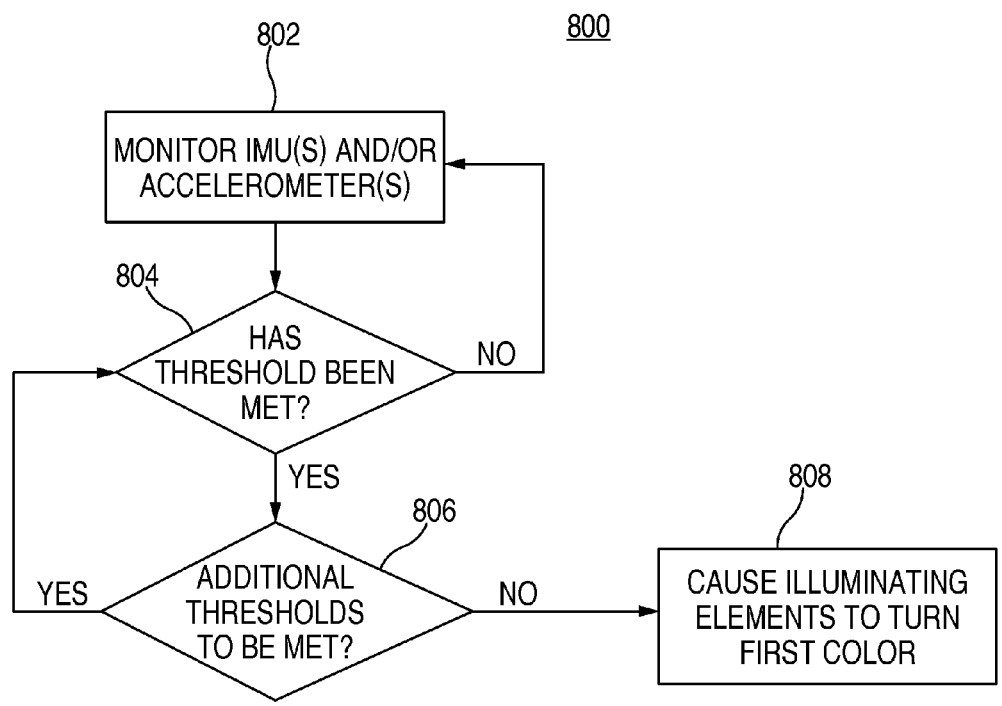
FIG. 14 is an illustrative flowchart of another exemplary process for providing feedback to a user throwing a ball in accordance with various embodiments.

FIG. 14 is an illustrative flowchart of another exemplary process for providing feedback to a user throwing a ball in accordance with various embodiments. Process 800 may begin at step 802. At step 802, IMU(s) 130 and/or accelerometer(s) 132 may be monitored. For example, outputs from IMU(s) 130 and/or accelerometer(s) 132 may be monitored. The various types of outputs may correspond to a velocity, horizontal displacement, vertical displacement, and/or spin rate of ball 100, for example.

At step 804, a determination may be made as to whether a threshold for an output monitored by IMU(s) 130 and/or accelerometer(s) 132 has been met. For example, processor(s) 136 may monitor outputs of IMU(s) 130 and/or accelerometer(s) 132 to determine if ball 100 has a spin rate associated with a selected pitch type. As an illustrative example, a 4-Seam Fastball, as seen in Table 1, may have a spin rate greater than 2200 RPMs. At step 804, it may be determined whether a spin rate of ball 100 is greater than 2200 RPMs. This determination may be made by detecting whether an output from IMU(s) 130 and/or accelerometer(s) 132 a spin rate of ball 100 is greater than 2200 RPMS.

If, at step 804, the threshold value for a particular parameter monitored has not been met, then processor 800 returns to step 802, and the parameter may continue to be monitored. For example, if a user is attempting to throw ball 100 as a 4-Seam Fastball, the detected output from IMU(s) 130 and/or accelerometer(s) 132 may initially indicate that ball 100 has a spin rate of 1000 RPMs. In this scenario, processor(s) 136 may continue to monitor the outputs from IMU(s) 130 and/or accelerometer(s) 132 as 1000 RPMs is less than the threshold value for a spin rate of a 4-Seam Fastball that has been selected to be thrown.

If, however, at step 804 the threshold value for a particular parameter has been met, then processor 800 may proceed to step 806. For example, IMU(s) 130 and/or accelerometer(s) 132 may detect that the spin rate of ball 100 is greater than the threshold value 2200 RPMs. At step 806, a determination is made as to whether or not other threshold values for additional parameters are to be met. If there are other values to be met for a particular pitch, then process 800 may return to step 804. Continuing the example mentioned previously, after it is determined that ball 100 has a spin rate greater than 2200 RPM, processor(s) 136 may also attempt to determine if the velocity of ball 100 is between the predefined values for a 4-Seam Fastball, 88-98 mph. If processor(s) 136 determine, based on outputs from IMU(s) 130 and/or accelerometer(s) 132, that the velocity of ball 100 is less than 88 mph, for example, then processor(s) 136 may continue to monitor the outputs from IMU(s) 130 and/or accelerometer(s) 132 until it is determined that baseball has a velocity greater than 88 mph, but less than 98 mph.

However, if at step 806 it is determined that all of the threshold values for any needed parameter for the selected pitch has been met, process 800 may proceed to step 808. At step 808, processor(s) 136 of ball 100 may cause illuminating elements 120 and/or 122 on ball 100 to turn a first color. For example, illuminating elements 120 and/or 122 may turn green to indicate to the individual ball 100 was thrown correctly. This may allow a user to have substantially immediate feedback with regards to the quality of the pitch they are trying to throw, and may allow a user to make substantially quick adjustments to improve the quality of the pitches they throw.

In some embodiments, however, instead of, or in addition to, causing illuminating elements to turn a first color in response to the threshold value(s) being met, one or more additional indicators may be caused to perform an action. For example, one or more speakers or transducers may output an audible tone in response to the threshold value(s) being met. In some embodiments, some threshold values being met may cause illuminating elements to turn a first color while other threshold values being met may cause other indicators, such as an audio output, to be played. For example, in response to the spin rate for a selected pitch being met, illuminating elements 120 and/or 122 may turn a first color, while if the velocity threshold for the selected pitch has been met, an audible tone will be outputted.

Figure 15:
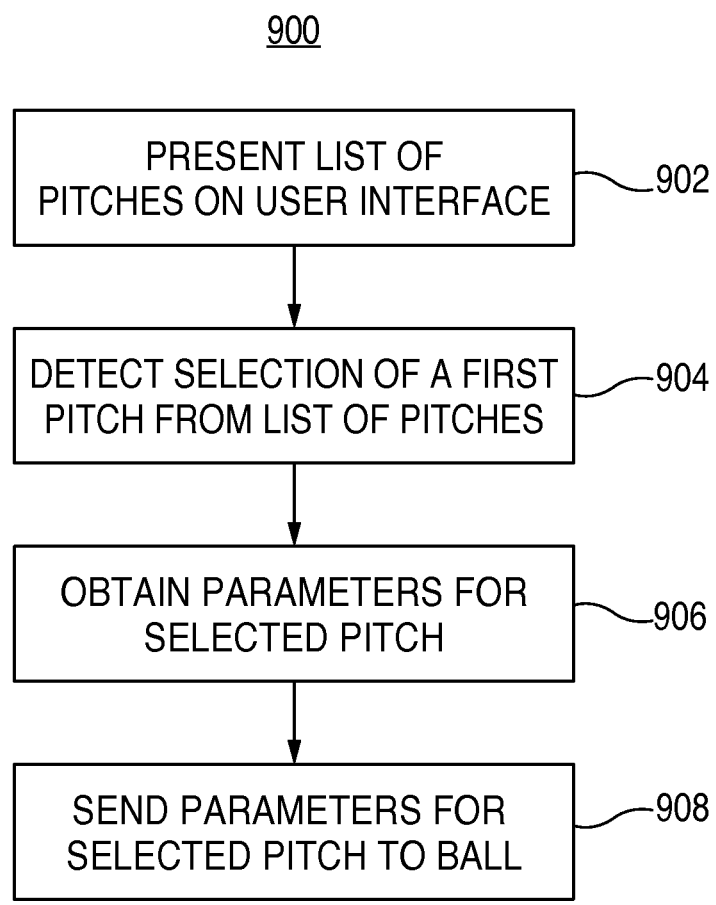
FIG. 15 is an illustrative flowchart of an exemplary process for providing parameters for a selected pitch to a ball in accordance with various embodiments.

FIG. 15 is an illustrative flowchart of an exemplary process for providing parameters for a selected pitch to a ball in accordance with various embodiments. Process 900 may begin at step 902. At step 902, a list of pitches may be presented on a user interface displayed on user device 450. For example, user interface 410 of FIG. 7 may present pitches 414, 416, 418, 422, 424, and 426 thereon. Parameters, including threshold value and/or acceptable ranges for each listed pitch may be stored in memory 454 on user device 450. In some embodiments, the parameters may correspond to a pitch's velocity, horizontal displacement, vertical displacement, and/or spin rate, however additional parameters may be used or inputted to user device 450.

At step 904, a selected of a first pitch from presented list of pitched may be detected. Display 466 may, in some embodiments, be a touch screen. A user may interact with display 466 by, for example, touching display 466 to select items or content displayed thereon. For example, user interface 410 may determine that a user has touched display 466 in a certain region corresponding to where a pitch, such as pitch 414, is currently being displayed. In response to determining that display 466 has been touched or interacted with about the certain region where a pitch is displayed, user device 450 may instruct display 466 to present user interface 410 including highlight 412 about pitch 414, indicating to the user that that pitch has been selected.

At step 906, parameters for the pitch selected a step 904, may be obtained. For example, parameters, such a threshold values or ranges for a pitches velocity, horizontal displacement, vertical displacement, and/or spin rate, may be obtained from memory/storage 454 on user device 450. In some embodiments, step 906 and step 904 may occur at a substantially same time.

At step 908, the parameters obtained from memory/storage 454 on user device 450 for the selected pitch may be sent to ball 100. For example, once obtained, communications circuitry 456 may transmit the parameters to ball 100 using communications link 420. In some embodiments, communications link 420 may be established prior to sending the parameters obtained at step 906. However, in some embodiments, communications link 420 may be established in response to user device attempting to send parameters for a selected pitch to ball 100.

Figure 16:
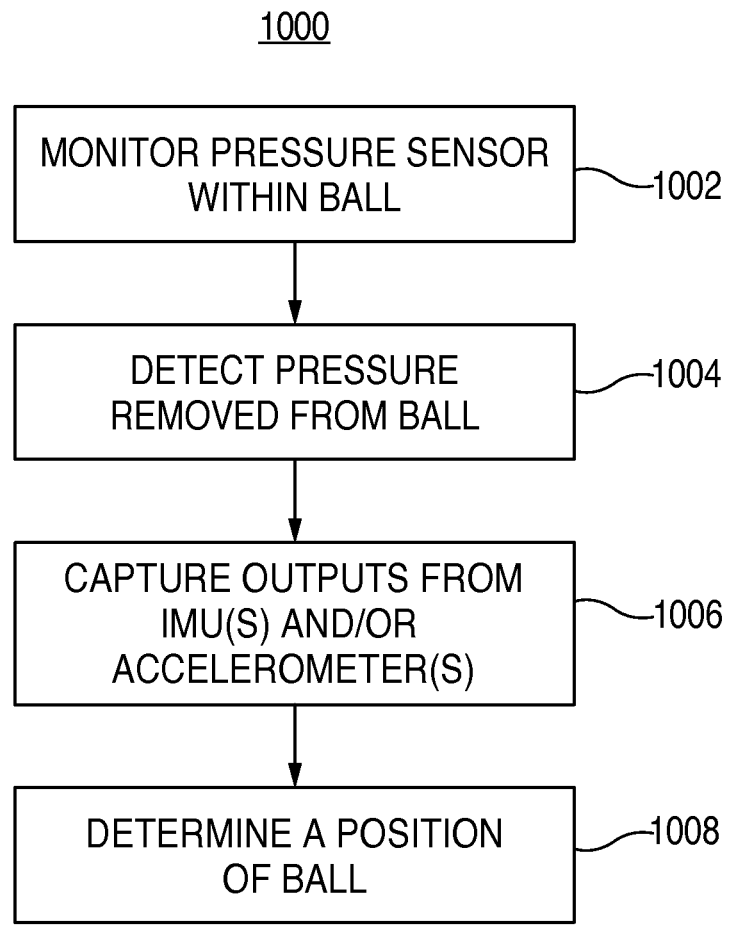
FIG. 16 is an illustrative flowchart of an exemplary process for determining a release point of a ball in accordance with various embodiments.

FIG. 16 is an illustrative flowchart of an exemplary process for determining a release point of a ball in accordance with various embodiments. Process 1000 may begin at step 1002. At step 1002, one or more pressure sensors within ball 100 may be monitored. For example, pressure sensors within ball 100 may detect when a user applies pressure to cover portions 102*a*, 102*b*.

At step 1004, the one or more pressure sensors within ball 100 may detect that pressure has been removed from ball 100. For example, the one or more pressure sensors that are being monitored will detect that pressure is no longer being applied to cover portions 102*a*, 102*b*. In some embodiments, the one or more pressure sensors may detect when pressure being applied to ball 100 has changed. For example, the one or more pressure sensors may detect when a user has changed the orientation or amount of pressure applied to cover portions 102*a*, 102*b*.

At step 1006, outputs from IMU(s) 130 and/or accelerometer(s) 1006 may be captured in response to detecting that pressure is no longer being applied to ball 100. For example, after the one or more pressure sensors determine that pressure is no longer being applied to cover portions 102*a*, 102*b* of ball 100, a signal may be sent to processor(s) 136 to capture a reading of IMU(s) 130 and/or accelerometer(s) 132 at that point in time.

At step 1008, a position of ball 100 may be determined based on the captured outputs from IMU(s) 130 and/or accelerometer(s) 132. For example, an amount of gravitational force on ball 100 may be determined so that a height of ball 100 (e.g., above pitching mound 206) may be determined. Thus, a height of release of ball 100 may be detected for ball 100 so that a pitcher throwing ball 100 is able to monitor the consistency of their release point. Persons of ordinary skill in the art will recognize that other parameters may be measured to determine lateral position of ball 100 in addition to a height above a pitcher's mound, such that a complete three-dimensional reconstruction of a pitcher's release point of ball 100 may be ascertained.

Figure 17:
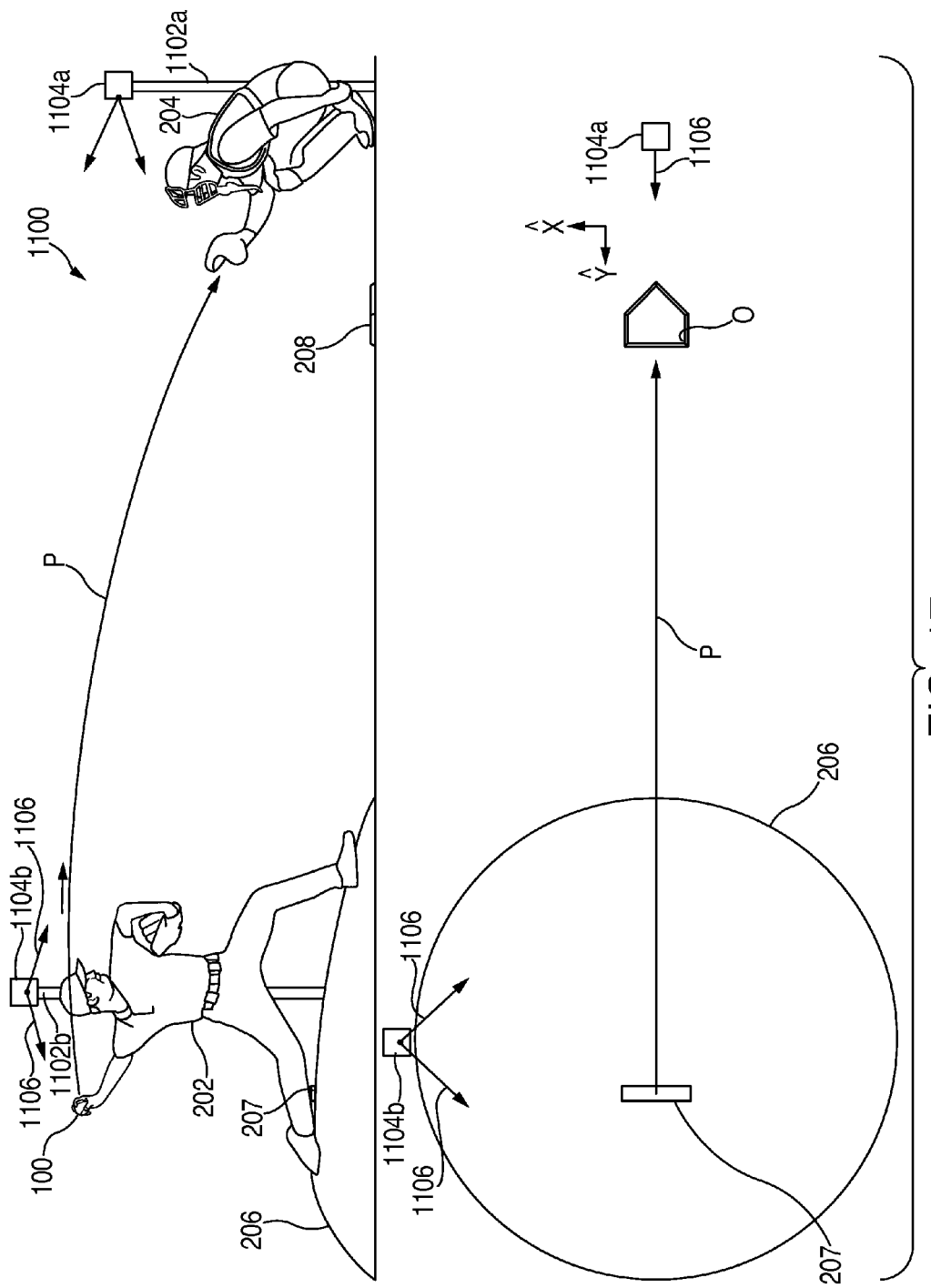
FIG. 17 is an illustrative diagram of a system for tracking a ball being thrown in accordance with various embodiments.

FIG. 17 is an illustrative diagram of a system for tracking a ball being thrown in accordance with various embodiments. System 1100 includes, in some embodiments, a first detection unit 1104*a* and second detection unit 1104*b*. First detection unit 1104*a* may be located proximate to home plate 208 such that it is directed at pitcher 202 throwing ball 100. Second detection unit 1104*b* may be located proximate pitching mound 206, and may be pointed at pitcher 202 perpendicular to the direction that ball 100 will be thrown. Persons of ordinary skill in the art will recognize that any number of detection units 1104a, 1104b may be included within system 1100, and the use of two detection units 1104a, 1104b is merely exemplary.

In some embodiments, detection units 1104a and 1104b may be positioned at any suitable location such that detection units 1104a and 1104b may analyze and track path P of ball 100. For example, detection unit 1104b may be placed on either side of pitcher's mound 206 such that it may monitor and/or track ball 100 when it is thrown along an x-y plane. Thus, detection unit 1104b may track a horizontal motion of ball 100. Detection unit 1104a may, in some embodiments, be placed behind home plate or behind pitcher's mound 206 such that it may monitor and/or track ball 100 when it is thrown along a y-z plane. Thus, detection unit 1104a may track vertical motion of ball 100. Detection units 1104a and 1104b may also include processing circuitry and communications circuitry such that they may process the motion information of ball 100 and transmit that information to a user device, such as user device 450, to reconstruct and/or analyze the motion of ball 100 as it is thrown. In some embodiments, the motion information obtained from detection units 1104a and 1104b may be combined with rotational motion information obtained from IMU(s) 130 within ball 100 to reconstruct and obtain data corresponding to how ball 100 is being thrown.

Detection units 1104a and 1104b, in some embodiments, may include motion tracking circuitry such as image capturing components operable to capture images and/or video of ball 100 as it is thrown. In some embodiments, detection units 1104a and 1104b may include radar technology such as Doppler and/or Sonar radar systems. However, persons of ordinary skill in the art will recognize that any other suitable monitoring technology may be used within detection units 1104a and 1104b, and the aforementioned is merely exemplary.

Detection units 1104a and 1104b may be mounted on any suitable stand or tower. For example, detection unit 1104a may be mounted on stand 1102a while detection unit 1104b may be mounted on stand 1102b. Stands 1102a and 1102b may be tripod stands made of a plastic or low-weight metal such as aluminum. This may allow stands 1102a and 1102b to be easily transportable. Detection units 1104a and 1104b may be mounted at a top end of stands 1102a and 1102b, and may be capable of being removed or detached from stands 1102a and 1102b.

Each detection unit may be capable of capturing motion information along a line of sight 1106. For example, detection unit 1104a may capture motion information of ball 100 along line of sight 1106 oriented along a y-z plane. This may enable detection unit 1104a to capture vertical motion information of ball 100 such that a user may be able to determine a change in vertical displacement of ball 100 along its path P. As another example, detection unit 1104b may capture motion information of ball 100 along line of sight 1106 oriented along a x-y plane. This may enable detection unit 1104b to capture horizontal motion information of ball 100 such that a user may able to determine a change in horizontal displacement of ball 100 along its path P. However, persons of ordinary skill in the art will recognize that additional detection units may be used within system 1100 which may be able to track motion along other axes, single axis, or at different positions. For example, a detection unit may monitor horizontal motion information of ball 100 at a release point proximate to pitcher 202, and another detection unit may monitor horizontal motion information of ball 100 at a capture point proximate to catcher 204 and/or home plate 208.

It should be appreciated that the various embodiments described above can be implemented by software, but can also be implemented in hardware or a combination of hardware and software. The various systems described above can also be embodied as computer readable code on a computer readable medium. The computer readable medium can be any data storage device that can store data, and that can thereafter be read by a computer system. Examples of computer readable mediums include read-only memory, random-access memory, CD-ROMs, DVDs, magnetic tape, and optical data storage devices. The computer readable medium can also be distributed over network-coupled computer systems so that the computer readable code is stored and executed in a distributed fashion.

The above described embodiments of the invention are presented for purposes of illustration and not of limitation.

What is claimed is:

1. A method for providing feedback to an individual throwing a ball, the method comprising: receiving a selection of a type of pitch for a ball to be thrown as; obtaining at least one parameter corresponding to the selected pitch type; monitoring at least one pressure sensor located within the ball; detecting, based on monitoring the at least one pressure sensor, an absence of pressure; determining, in response to detecting the absence of pressure, a three-dimensional spatial location of the ball at substantially the same instant that the absence of pressure was detected; monitoring, in response to detecting the absence of pressure, at least one additional sensor located within the ball; determining that the at least one additional sensor has detected the at least one parameter corresponding to the selected type of pitch; and causing at least one illuminating element located on a surface of the ball to turn a first color in response to the at least one parameter being detected.

2. The method of claim 1, wherein the at least one parameter for the selected type of pitch of the ball to be thrown comprises at least one of: a spin rate; an amount of vertical displacement; an amount of horizontal displacement; and velocity.

3. The method of claim 1, wherein the at least one additional sensor comprises at least one of: an inertial measurement unit; a gyroscope; and an accelerometer.

4. The method of claim 1, wherein determining further comprises: detecting that the output from the at least one additional sensor has exceeded a predefined threshold for the at least one parameter.

5. The method of claim 1, further comprising: causing at least one audio producing element to produce an audio tone in response to the at least one parameter being detected.

* * * * *